(12) United States Patent
Scheib et al.

(10) Patent No.: US 10,201,348 B2
(45) Date of Patent: Feb. 12, 2019

(54) SURGICAL STAPLER CARTRIDGE WITH COMPRESSION FEATURES AT STAPLE DRIVER EDGES

(71) Applicant: Ethicon Endo-Surgery, LLC, Guaynabo, PR (US)

(72) Inventors: Charles J. Scheib, Loveland, OH (US); Jeffrey S. Swayze, West Chester, OH (US)

(73) Assignee: Ethicon LLC, Guaynabo, PR (US)

( * ) Notice: Subject to any disclaimer, the term of this patent is extended or adjusted under 35 U.S.C. 154(b) by 513 days.

(21) Appl. No.: 14/811,087

(22) Filed: Jul. 28, 2015

(65) Prior Publication Data

US 2017/0027568 A1   Feb. 2, 2017

(51) Int. Cl.
| | | |
|---|---|---|
| *A61B 17/04* | (2006.01) | |
| *A61B 17/10* | (2006.01) | |
| *A61B 17/072* | (2006.01) | |
| *A61B 17/00* | (2006.01) | |
| *A61B 17/29* | (2006.01) | |

(52) U.S. Cl.
CPC ............ *A61B 17/07207* (2013.01); *A61B 2017/00398* (2013.01); *A61B 2017/00862* (2013.01); *A61B 2017/07278* (2013.01); *A61B 2017/2927* (2013.01); *A61B 2017/2929* (2013.01)

(58) Field of Classification Search
CPC ............ A61B 17/068; A61B 17/07292; A61B 17/105; A61B 17/0644; A61B 2017/2905; A61B 2017/00862; A61B 2017/0464
USPC .............................. 227/175.1–182.1; 606/142
See application file for complete search history.

(56) References Cited

U.S. PATENT DOCUMENTS

| | | | |
|---|---|---|---|
| 4,805,823 A | | 2/1989 | Rothfuss |
| 4,930,674 A | * | 6/1990 | Barak .................. A61B 17/072 227/179.1 |
| 5,415,334 A | | 5/1995 | Williamson et al. |
| 5,465,895 A | | 11/1995 | Knodel et al. |
| 5,551,622 A | * | 9/1996 | Yoon .................... A61B 17/072 227/176.1 |

(Continued)

FOREIGN PATENT DOCUMENTS

| | | |
|---|---|---|
| EP | 1 785 098 A2 | 5/2007 |
| EP | 1 785 101 A2 | 5/2007 |
| EP | 2 374 419 A2 | 10/2011 |

OTHER PUBLICATIONS

U.S. Appl. No. 14/226,142, filed Mar. 26, 2014.

(Continued)

*Primary Examiner* — Robert Long
(74) *Attorney, Agent, or Firm* — Frost Brown Todd LLC

(57) ABSTRACT

An apparatus includes a body, a shaft assembly, an end effector, and a staple cartridge. The end effector includes an anvil and a lower jaw. The anvil is pivotable toward the lower jaw to clamp tissue. The staple cartridge is coupled with the lower jaw. The staple cartridge includes a deck, a plurality of staples, and a plurality of staple drivers. The deck faces the anvil. The staples are positioned in a plurality of staple openings formed through the deck. The staple drivers are configured to drive the staples out of the staple openings. Each staple driver of the plurality of staple drivers includes a staple driver body. At least a portion of the staple drivers further include a compressible feature extending from the staple driver body toward the anvil.

19 Claims, 20 Drawing Sheets

(56) References Cited

U.S. PATENT DOCUMENTS

| | | |
|---|---|---|
| 5,597,107 A | 1/1997 | Knodel et al. |
| 5,632,432 A | 5/1997 | Schulze et al. |
| 5,673,840 A | 10/1997 | Schulze et al. |
| 5,704,534 A | 1/1998 | Huitema et al. |
| 5,792,135 A | 8/1998 | Madhani et al. |
| 5,814,055 A | 9/1998 | Knodel et al. |
| 5,817,084 A | 10/1998 | Jensen |
| 5,878,193 A | 3/1999 | Wang et al. |
| 6,231,565 B1 | 5/2001 | Tovey et al. |
| 6,364,888 B1 | 4/2002 | Niemeyer et al. |
| 6,783,524 B2 | 8/2004 | Anderson et al. |
| 6,978,921 B2 | 12/2005 | Shelton et al. |
| 7,000,818 B2 | 2/2006 | Shelton et al. |
| 7,143,923 B2 | 12/2006 | Shelton et al. |
| 7,303,108 B2 | 12/2007 | Shelton |
| 7,367,485 B2 | 5/2008 | Shelton et al. |
| 7,380,695 B2 | 6/2008 | Doll et al. |
| 7,380,696 B2 | 6/2008 | Shelton et al. |
| 7,404,508 B2 | 7/2008 | Smith et al. |
| 7,434,715 B2 | 10/2008 | Shelton et al. |
| 7,524,320 B2 | 4/2009 | Tierney |
| 7,691,098 B2 | 4/2010 | Wallace et al. |
| 7,694,864 B2 * | 4/2010 | Okada ................ A61B 17/1114 227/175.1 |
| 7,721,930 B2 | 5/2010 | McKenna et al. |
| 7,806,891 B2 | 10/2010 | Nowlin et al. |
| 8,210,411 B2 | 7/2012 | Yates et al. |
| 8,408,439 B2 | 4/2013 | Huang et al. |
| 8,453,914 B2 | 6/2013 | Laurent et al. |
| 8,720,766 B2 | 5/2014 | Hess et al. |
| 8,955,732 B2 * | 2/2015 | Zemlok ................ A61B 17/072 227/176.1 |
| 8,998,060 B2 * | 4/2015 | Bruewer .......... A61B 17/00491 227/176.1 |
| 9,839,420 B2 * | 12/2017 | Shelton, IV ......... A61B 17/068 |
| 2008/0078800 A1 * | 4/2008 | Hess ................ A61B 17/0644 227/175.1 |
| 2008/0312687 A1 * | 12/2008 | Blier .................. A61B 17/0644 606/219 |
| 2009/0277949 A1 * | 11/2009 | Viola ................... A61B 17/072 227/178.1 |
| 2011/0248064 A1 * | 10/2011 | Marczyk .......... A61B 17/07207 227/114 |
| 2012/0132450 A1 | 5/2012 | Timm et al. |
| 2012/0138660 A1 | 6/2012 | Shelton et al. |
| 2012/0199630 A1 | 8/2012 | Shelton |
| 2012/0199631 A1 | 8/2012 | Shelton et al. |
| 2012/0199632 A1 | 8/2012 | Spivey et al. |
| 2012/0199633 A1 | 8/2012 | Shelton et al. |
| 2012/0203247 A1 | 8/2012 | Shelton et al. |
| 2012/0205421 A1 | 8/2012 | Shelton |
| 2012/0211546 A1 | 8/2012 | Shelton |
| 2013/0012957 A1 | 1/2013 | Shelton et al. |
| 2013/0214030 A1 * | 8/2013 | Aronhalt ............. A61B 17/068 227/176.1 |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239042 A1 | 8/2014 | Simms et al. |
| 2014/0239043 A1 | 8/2014 | Simms et al. |
| 2014/0239044 A1 | 8/2014 | Hoffman |
| 2014/0243801 A1 | 8/2014 | Fanelli et al. |

OTHER PUBLICATIONS

U.S. Appl. No. 14/314,108, filed Jun. 25, 2014.
U.S. Appl. No. 14/314,125, filed Jun. 25, 2014.
International Search Report and Written Opinion dated Dec. 21, 2016 for Application No. PCT/US2016/042739, 15 pgs.
European Search Report and Written Opinion dated Dec. 15, 2016 for Application No. EP16181516.2, 10 pgs.

* cited by examiner

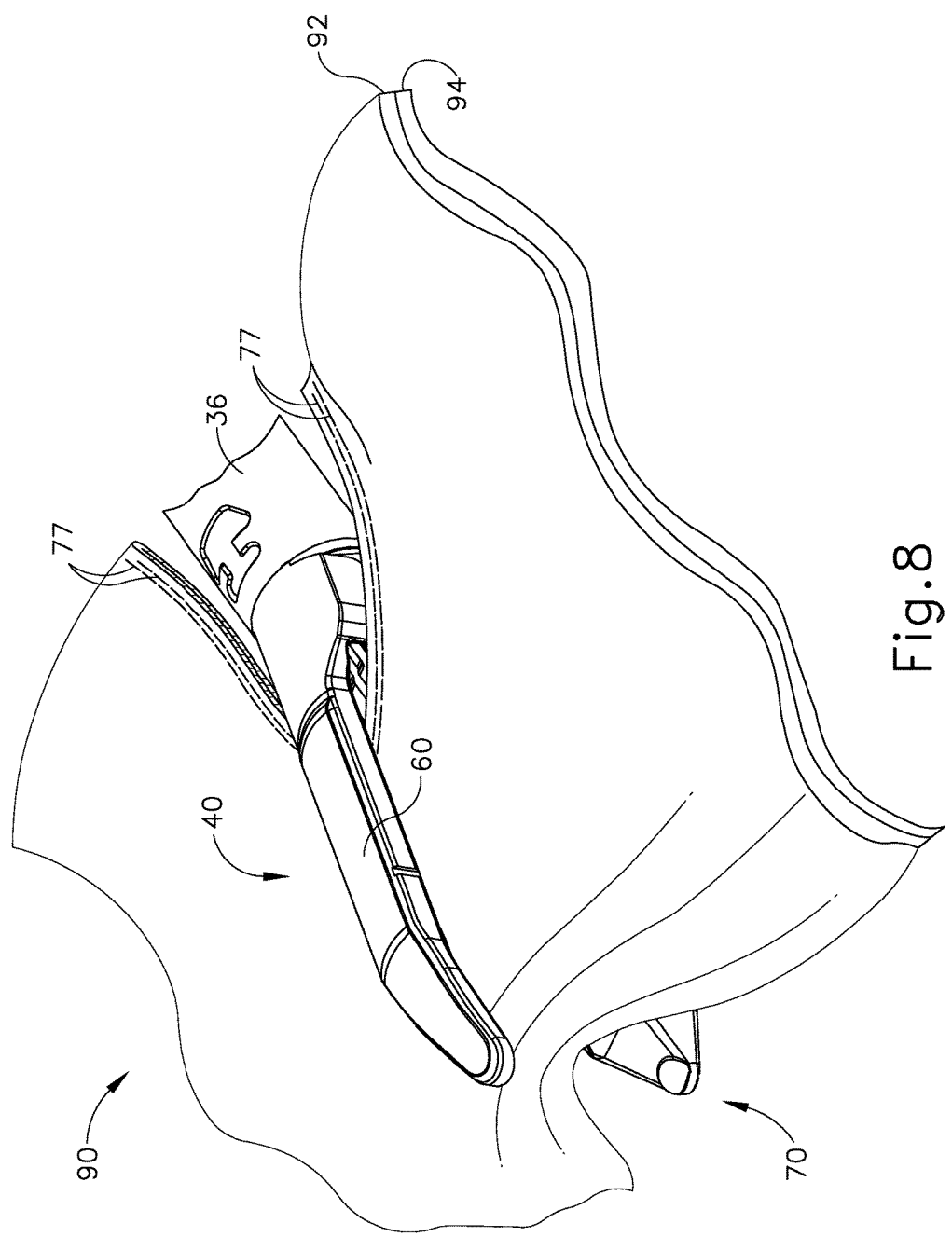

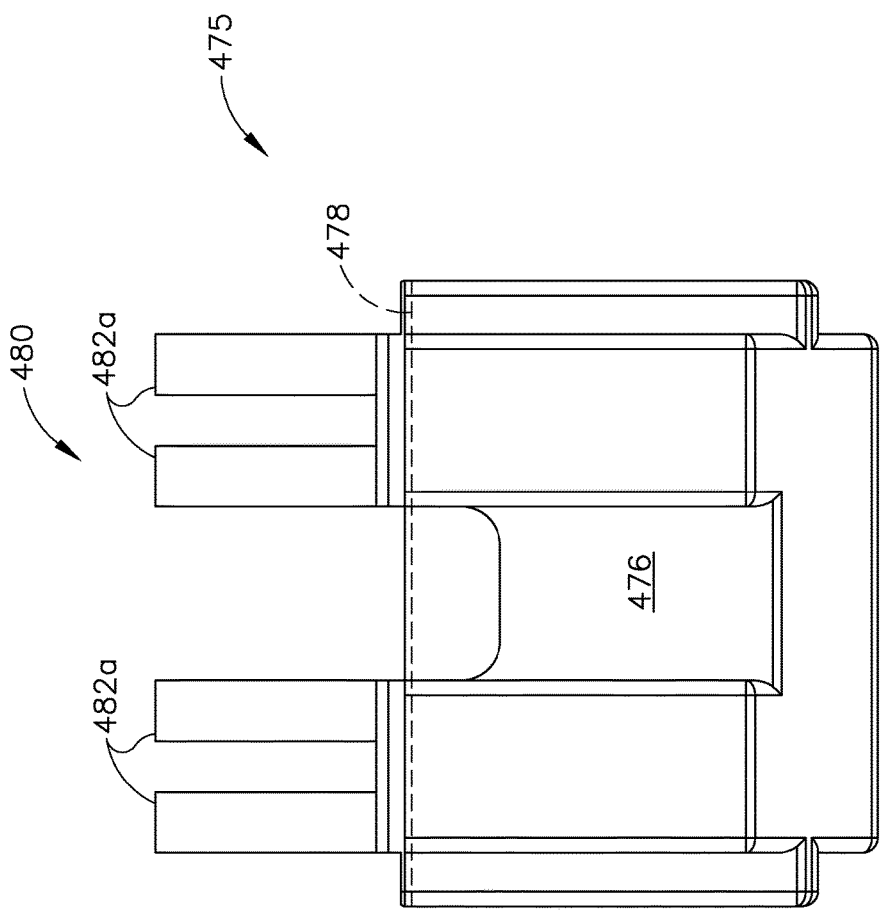

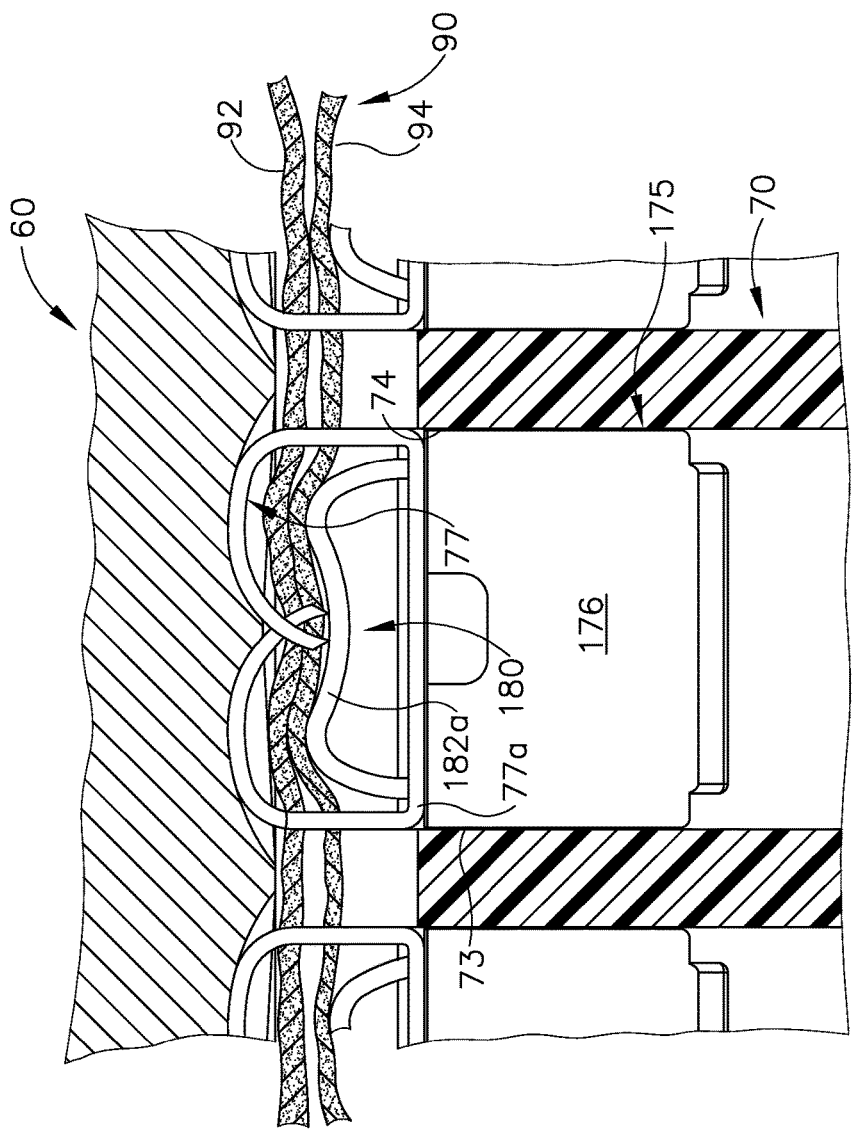

SURGICAL STAPLER CARTRIDGE WITH COMPRESSION FEATURES AT STAPLE DRIVER EDGES

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. Patent Pub. No. 2014/0243801, entitled "Surgical Instrument End Effector Articulation Drive with Pinion and Opposing Racks," published Aug. 28, 2014, now U.S. Pat. No. 9,186,142, issued Nov. 17, 2015; U.S. Patent Pub. No. 2014/0239041, entitled "Lockout Feature for Movable Cutting Member of Surgical Instrument," published Aug. 28, 2014, now U.S. Pat. No. 9,717,497, issued Aug. 1, 2017; U.S. Patent Pub. No. 2014/0239042, entitled "Integrated Tissue Positioning and Jaw Alignment Features for Surgical Stapler," published Aug. 28, 2014, now U.S. Pat. No. 9,517,065, issued Dec. 13, 2016; U.S. Patent Pub. No. 2014/0239036, entitled "Jaw Closure Feature for End Effector of Surgical Instrument," published Aug. 28, 2014, now U.S. Pat. No. 9,839,421, issued Dec. 12, 2017; U.S. Patent Pub. No. 2014/0239040, entitled "Surgical Instrument with Articulation Lock having a Detenting Binary Spring," published Aug. 28, 2014, now U.S. Pat. No. 9,867,615, issued Jan. 16, 2018; U.S. Patent Pub. No. 2014/0239043, entitled "Distal Tip Features for End Effector of Surgical Instrument," published Aug. 28, 2014; now U.S. Pat. No. 9,622, 746, issued Apr. 18, 2017; U.S. Patent Pub. No. 2014/0239037, entitled "Staple Forming Features for Surgical Stapling Instrument," published Aug. 28, 2014; now U.S. Pat. No. 10,092,292, issued Oct. 9, 2018; U.S. Patent Pub. No. 2014/0239038, entitled "Surgical Instrument with Multi-Diameter Shaft," published Aug. 28, 2014, now U.S. Pat. No. 9,795,379, issued Oct. 24, 2017; and U.S. Patent Pub. No. 2014/0239044, entitled "Installation Features for Surgical Instrument End Effector Cartridge," published Aug. 28, 2014, now U.S. Pat. No. 9,808,248, issued Nov. 7, 2017. The disclosure of each of the above-cited U.S. Patent Applications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 8 depicts a perspective view of the end effector of FIG. 3, positioned at tissue and having been actuated once in the tissue;

FIG. 12 depicts a side elevational view of another exemplary alternative staple driver that may be incorporated into a staple cartridge used in the end effector of FIG. 3;

FIG. 14C depicts a partial, cross-sectional side view of the end effector of FIG. 13C, taken along line 14C-14C of FIG. 13C, showing the staple in a second intermediate position.

Figure 1:
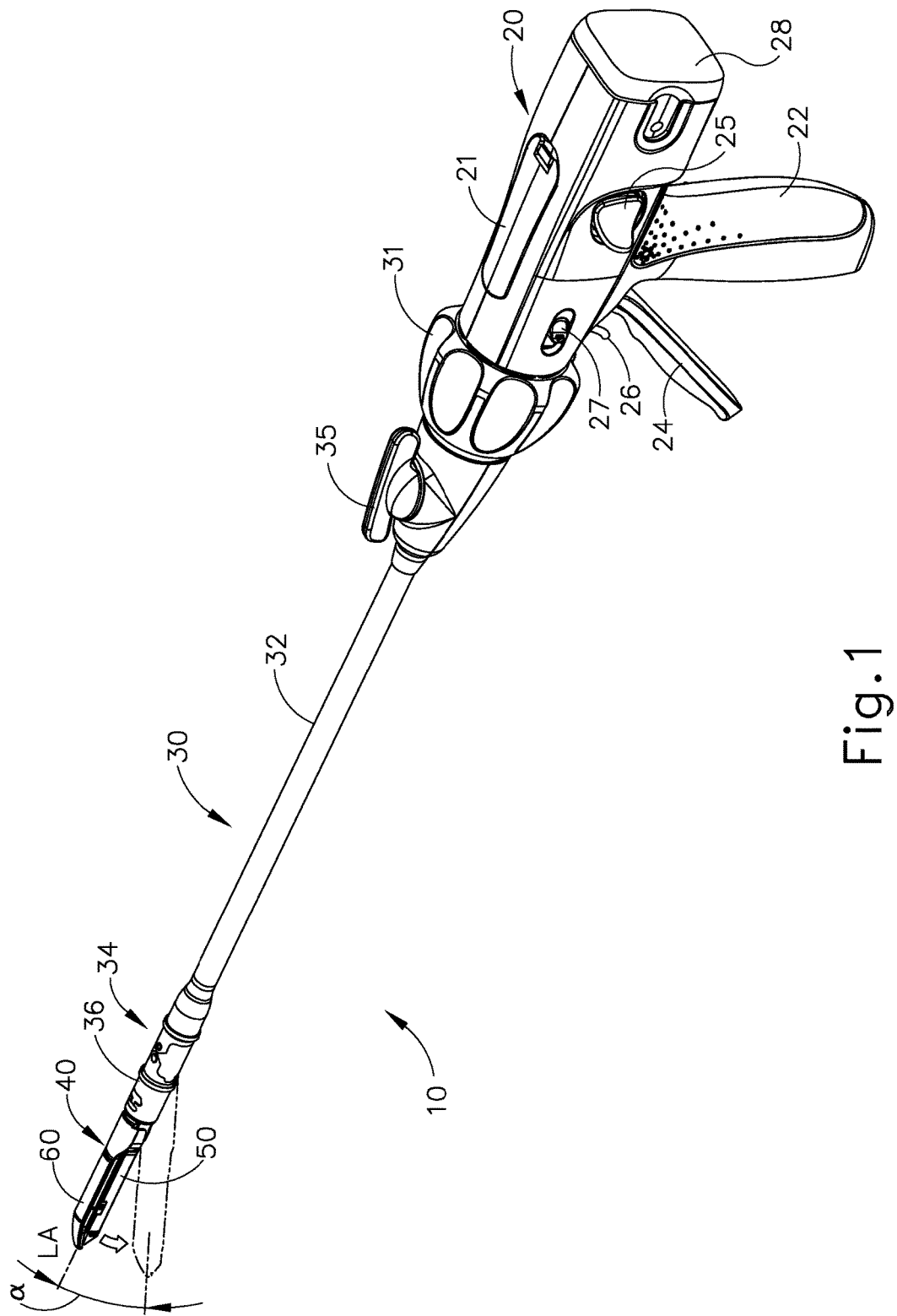
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

Figure 2:
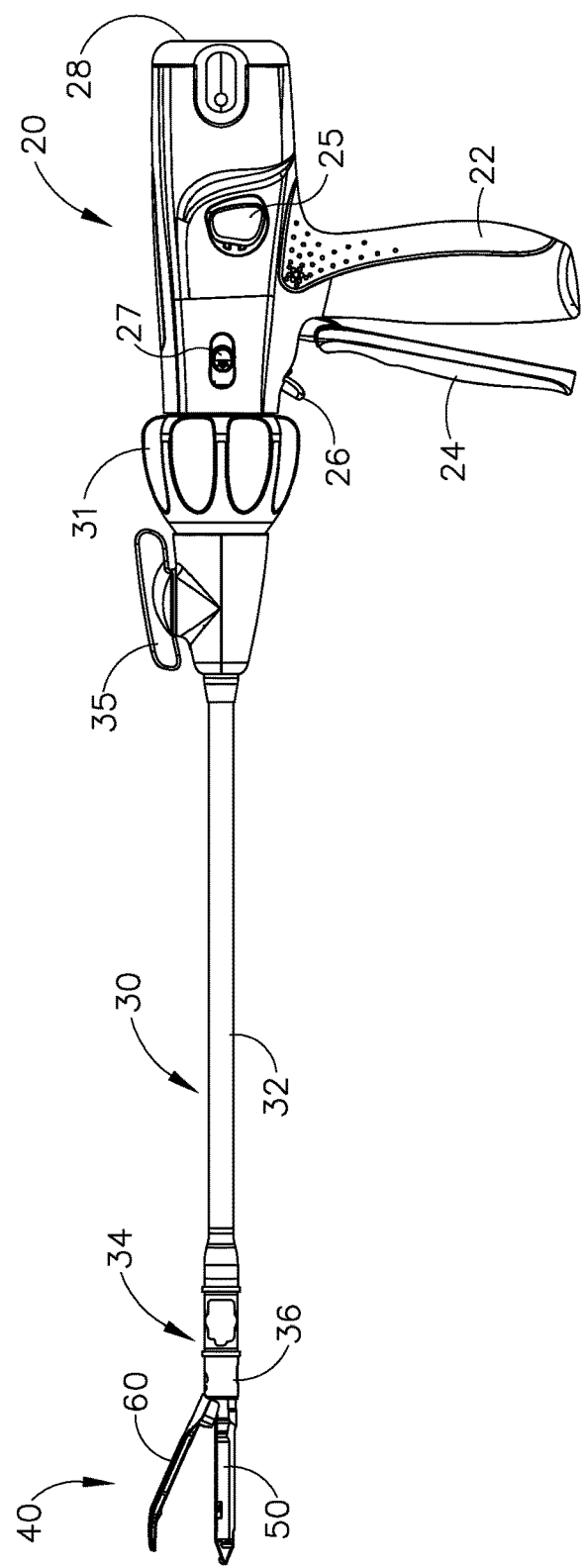
FIG. 2 depicts a side elevational view of the instrument of FIG. 1.

As shown in FIGS. 1-2, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes an anvil release button (25), a firing beam reverse switch (27), and a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

Figure 3:
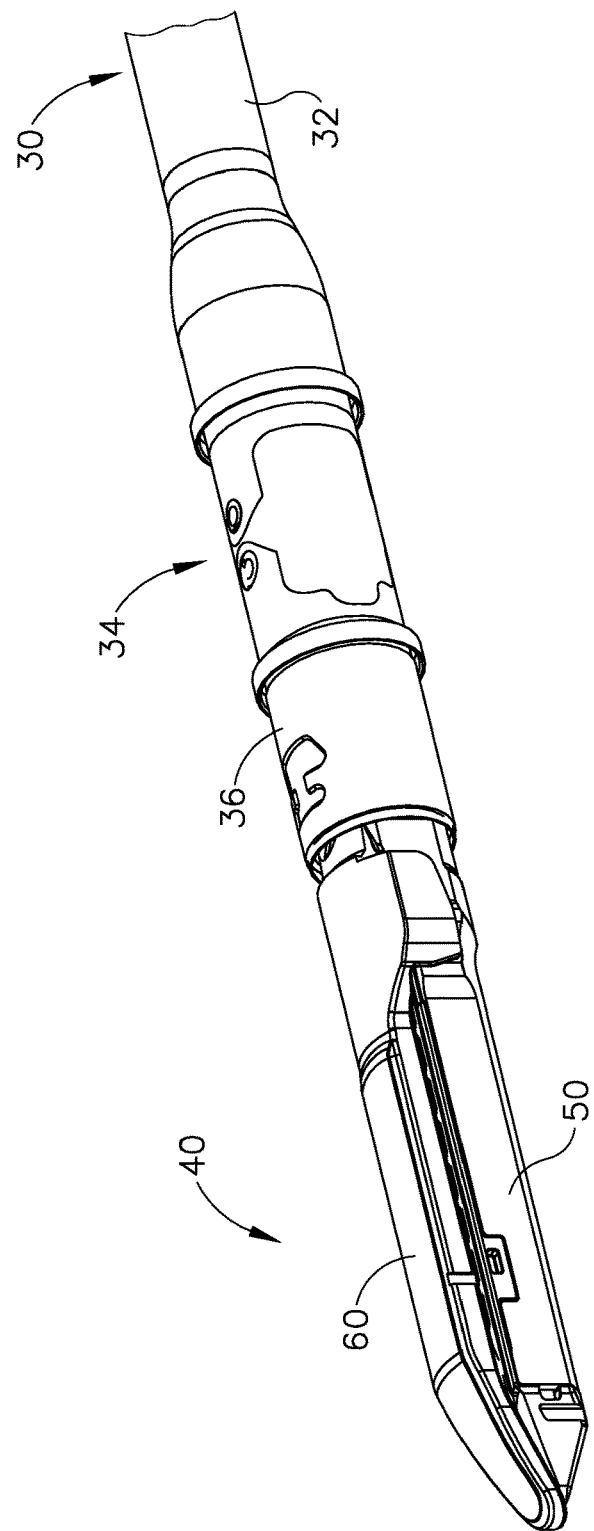
FIG. 3 depicts a perspective view of an end effector of the instrument of FIG. 1, with the end effector in a closed configuration.

As shown in FIGS. 1-3, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle (α). End effector (40) may thereby reach behind an organ or approach tissue from a desired angle or for other reasons. In some versions, articulation section (34) enables deflection of end effector (40) along a single plane. In some other versions, articulation section (34) enables deflection of end effector along more than one plane. In the present example, articulation is controlled through an articulation control knob (35) which is located at the proximal end of shaft assembly (30). Knob (35) is rotatable about an axis that is perpendicular to the longitudinal axis (LA) of shaft assembly (30). Closure ring (36) and end effector (40) pivot about an axis that is perpendicular to the longitudinal axis (LA) of shaft assembly (30) in response to rotation of knob (35). By way of example only, rotation of knob (35) clockwise may cause corresponding clockwise pivoting of closure ring (36) and end effector (40) at articulation section (34). Articulation section (34) is configured to communicate longitudinal translation of closure tube (32) to closure ring (36), regardless of whether articulation section (34) is in a straight configuration or an articulated configuration.

In some versions, articulation section (34) and/or articulation control knob (35) are/is constructed and operable in accordance with at least some of the teachings of U.S. Pub. No. 2014/0243801, entitled "Surgical Instrument End Effector Articulation Drive with Pinion and Opposing Racks," published Aug. 28, 2014, now U.S. Pat. No. 9,186,142, issued Nov. 17, 2015, the disclosure of which is incorporated by reference herein. Articulation section (34) may also be constructed and operable in accordance with at least some of the teachings of U.S. patent application Ser. No. 14/314,125, entitled "Articulation Drive Features for Surgical Stapler," filed Jun. 25, 2014, published as U.S. Patent Pub. No. 2015/0374360 on Dec. 31, 2015, the disclosure of which is incorporated by reference herein; and/or in accordance with the various teachings below. Other suitable forms that articulation section (34) and articulation knob (35) may take will be apparent to those of ordinary skill in the art in view of the teachings herein.

As shown in FIGS. 1-2, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). In some versions, rotation knob (31) is operable to selectively lock the angular position of shaft assembly (30) and end effector (40) relative to handle assembly (20) about the longitudinal axis (LA) of shaft assembly (30). For instance, rotation knob (31) may be translatable between a first longitudinal position, in which shaft assembly (30) and end effector (40) are rotatable relative to handle assembly (20) about the longitudinal axis (LA) of shaft assembly (30); and a second longitudinal position, in which shaft assembly (30) and end effector (40) are not rotatable relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. Pub. No. 2014/0239038, entitled "Surgical Instrument with Multi-Diameter Shaft," published Aug. 28, 2014, now U.S. Pat. No. 9,795,379, issued Oct. 24, 2017, the disclosure of which is incorporated by reference herein. Other suitable configurations for shaft assembly (30) will be apparent to those of ordinary skill in the art in view of the teachings herein.

B. Exemplary End Effector

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Pins (66) and slots (54) are shown in FIG. 5. Anvil (60) is pivotable toward and away from lower jaw (50) between an open position (shown in FIGS. 2 and 4) and a closed position (shown in FIGS. 1, 3, and 7A-7B). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 5, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. Pub. No. 2014/0239044, entitled "Installation Features for Surgical Instrument End Effector Cartridge," published Aug. 28, 2014, now U.S. Pat. No. 9,808,248, issued Nov. 7, 2017, the disclosure of which is incorporated by reference herein. Other suitable forms that lower jaw (50) may take will be apparent to those of ordinary skill in the art in view of the teachings herein.

Figure 4:
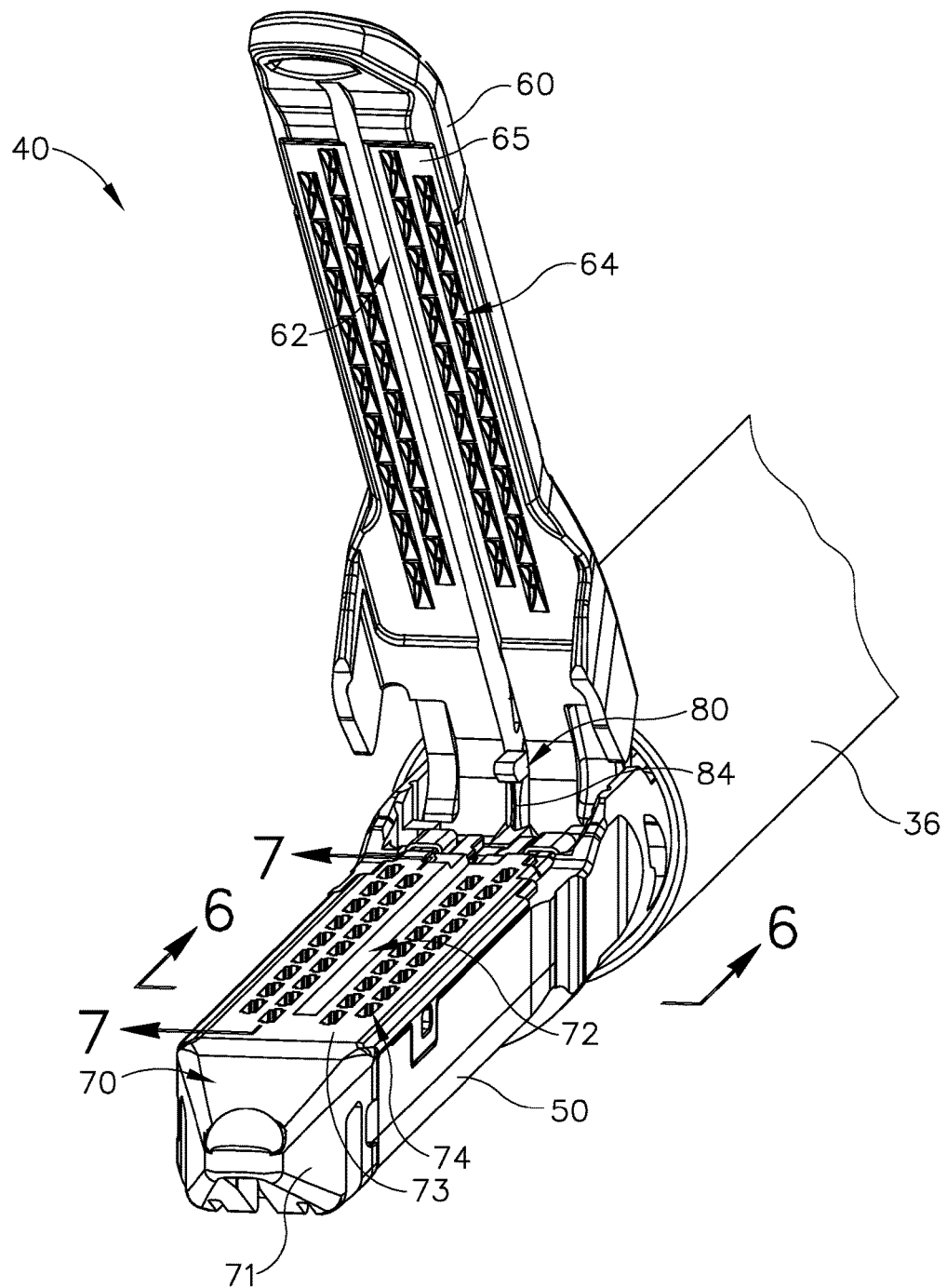
FIG. 4 depicts a perspective view of the end effector of FIG. 3, with the end effector in an open configuration.
Figure 5:
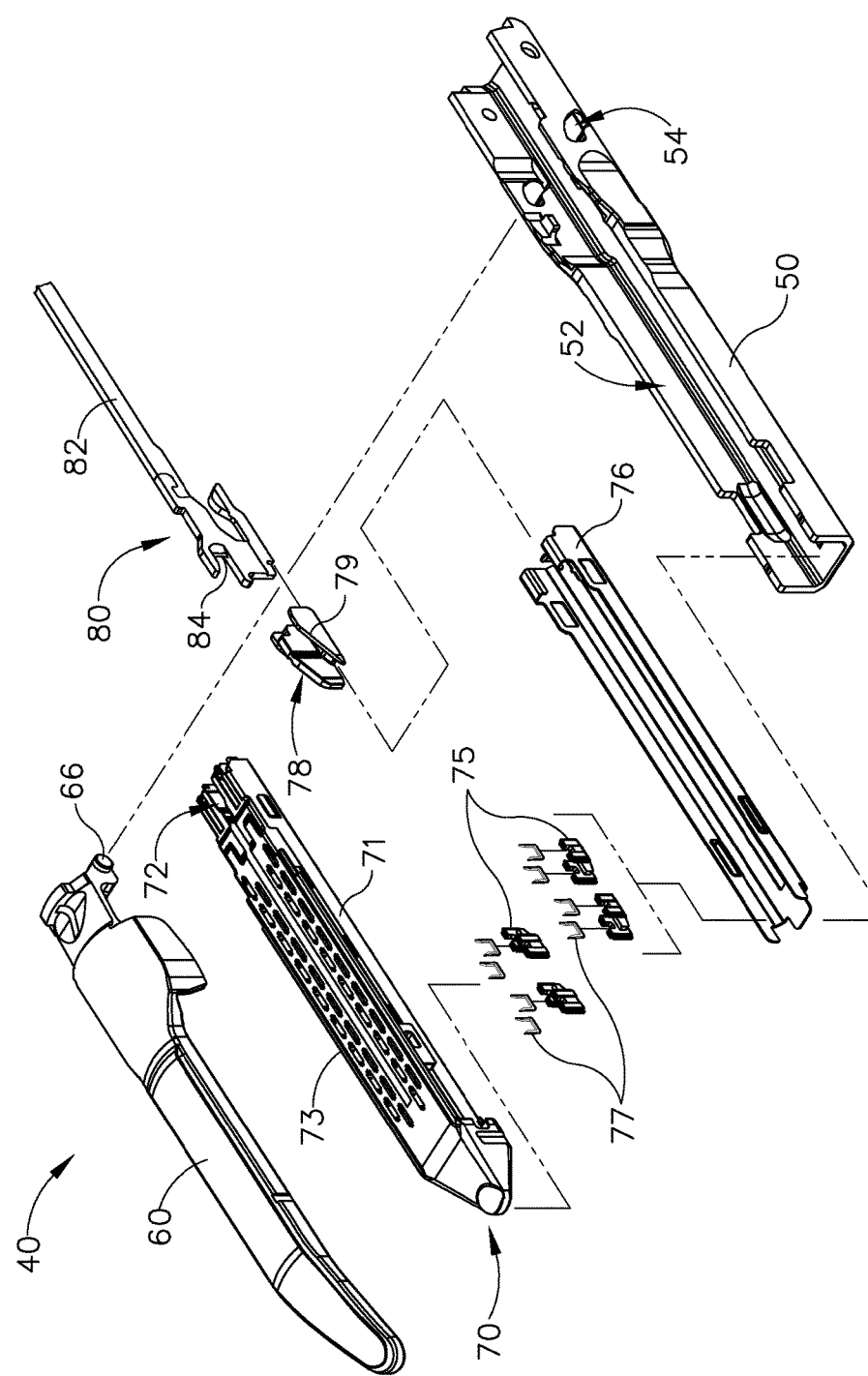
FIG. 5 depicts an exploded perspective view of the end effector of FIG. 3.
Figure 6:
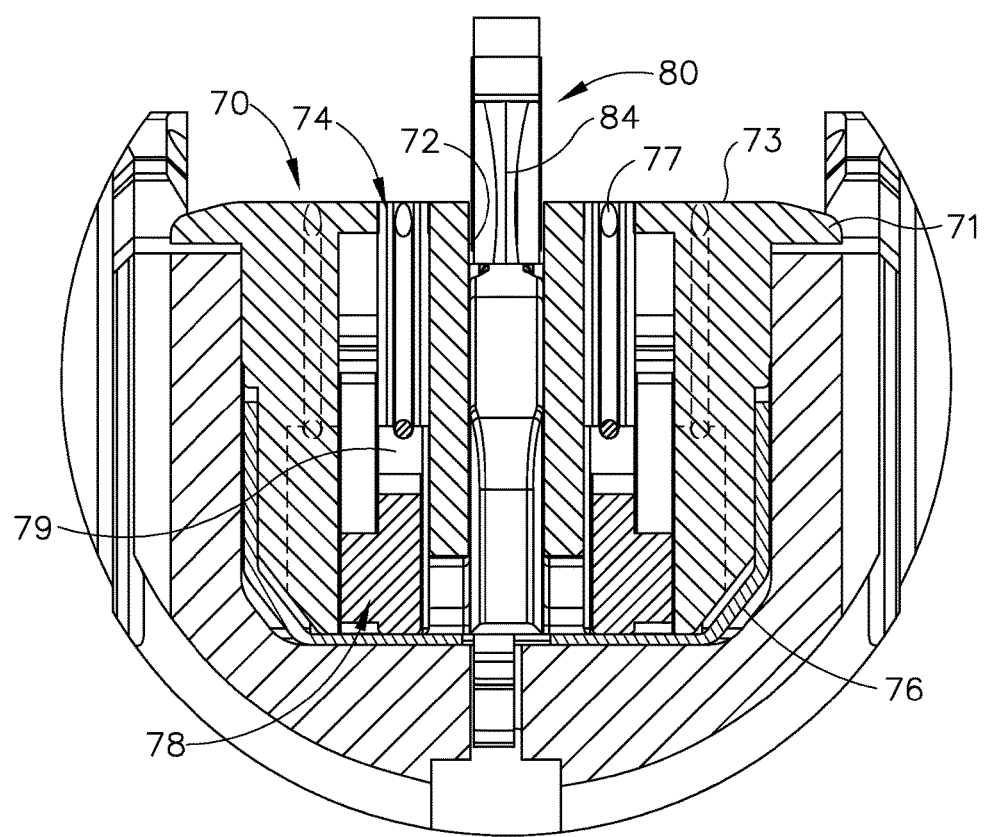
FIG. 6 depicts a cross-sectional end view of the end effector of FIG. 3, taken along line 6-6 of FIG. 4.
Figure 7A:
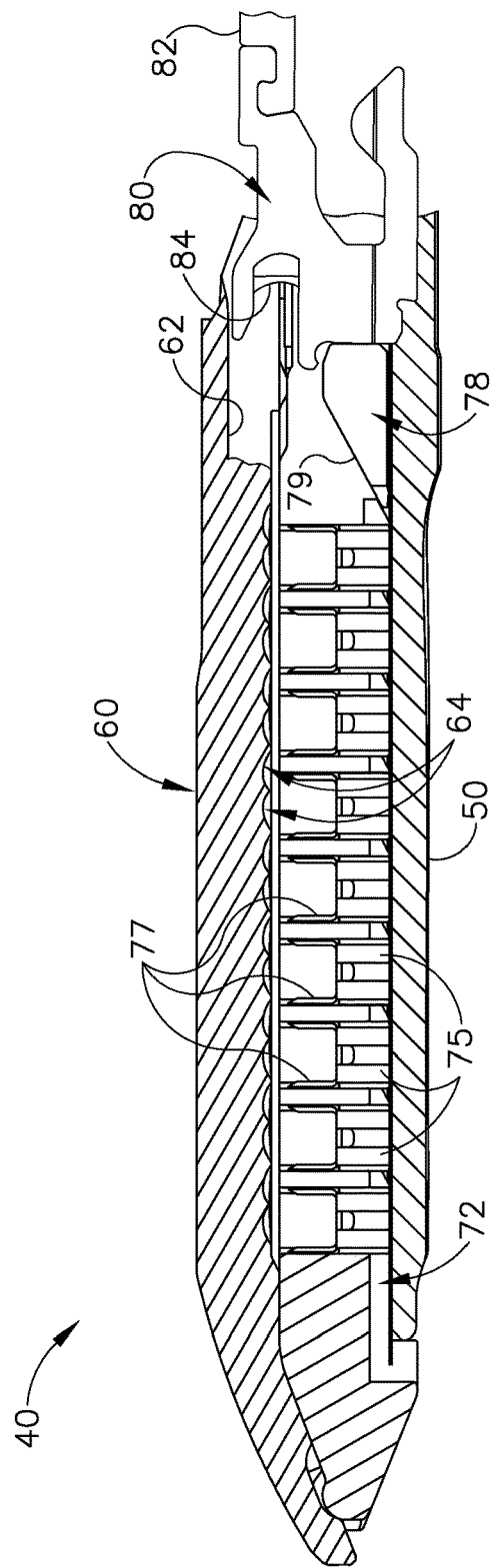
FIG. 7A depicts a cross-sectional side view of the end effector of FIG. 3, taken along line 7-7 of FIG. 4, with a firing beam in a proximal position.

As best seen in FIGS. 4-6, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (77) is positioned in each staple pocket (74). A staple driver (75) is also positioned in each staple pocket (74), underneath a corresponding staple (77), and above tray (76). As will be described in greater detail below, staple drivers (75) are operable to translate upwardly in staple pockets (74) to thereby drive staples (77) upwardly through staple pockets (74) and into engagement with anvil (60). Staple drivers (75) are driven upwardly by a wedge sled (78), which is captured between cartridge body (71) and tray (76), and which translates longitudinally through cartridge body (71). Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position as shown in FIG. 7A, staple drivers (75) are in downward positions and staples (77) are located in staple pockets (74). As wedge sled (78) is driven to the distal position shown in FIG. 7B by a translating knife member (80), wedge sled (78) drives staple drivers (75) upwardly, thereby driving staples (77) out of staple pockets (74) and into staple forming pockets (64). Thus, staple drivers (75) translate along a vertical dimension as wedge sled (78) translates along a horizontal dimension.

It should be understood that the configuration of staple cartridge (70) may be varied in numerous ways. For instance, staple cartridge (70) of the present example includes two longitudinally extending rows of staple pockets (74) on one side of channel (72); and another set of two longitudinally extending rows of staple pockets (74) on the other side of channel (72). However, in some other versions, staple cartridge (70) includes three, one, or some other number of staple pockets (74) on each side of channel (72). In some versions, staple cartridge (70) is constructed and operable in accordance with at least some of the teachings of U. U.S. Pub. No. 2014/0239042, entitled "Integrated Tissue Positioning and Jaw Alignment Features for Surgical Stapler," published Aug. 28, 2014, now U.S. Pat. No. 9,517,065, issued Dec. 13, 2016, the disclosure of which is incorporated by reference herein. In addition or in the alternative, staple cartridge (70) may be constructed and operable in accordance with at least some of the teachings of U.S. Pub. No. 2014/0239044, entitled "Installation Features for Surgical Instrument End Effector Cartridge," published Aug. 28, 2014, now U.S. Pat. No. 9,808,248, issued Nov. 7, 2017, the disclosure of which is incorporated by reference herein. Other suitable forms that staple cartridge (70) may take will be apparent to those of ordinary skill in the art in view of the teachings herein.

As best seen in FIG. 4, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (77) when staples (77) are driven through tissue and into anvil (60). In particular, staple forming pockets (64) are configured to bend the legs of staples (77) to secure the formed staples (77) in the tissue. Anvil (60) may be constructed in accordance with at least some of the teachings of U.S. Pub. No. 2014/0239042, entitled "Integrated Tissue Positioning and Jaw Alignment Features for Surgical Stapler," published Aug. 28, 2014, now U.S. Pat. No. 9,517,065, issued Dec. 13, 2016; at least some of the teachings of U.S. Pub. No. 2014/0239036, entitled "Jaw Closure Feature for End Effector of Surgical Instrument," published Aug. 28, 2014, now U.S. Pat. No. 9,839,421, issued Dec. 12, 2017; and/or at least some of the teachings of U.S. Pub. No. 2014/0239037, entitled "Staple Forming Features for Surgical Stapling Instrument," published Aug. 28, 2014, now U.S. Pat. No. 10,092,292, issued Oct. 9, 2018, the disclosure of which is incorporated by reference herein. Other suitable forms that anvil (60) may take will be apparent to those of ordinary skill in the art in view of the teachings herein.

Figure 7B:
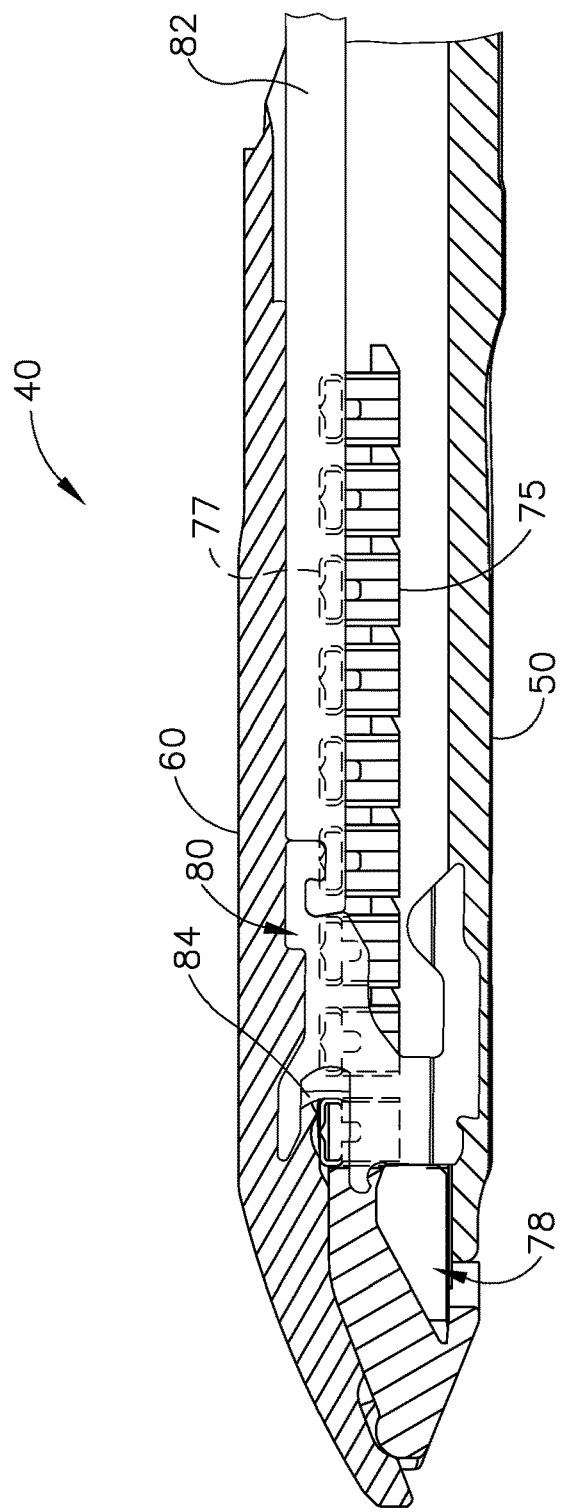
FIG. 7B depicts a cross-sectional side view of the end effector of FIG. 3, taken along line 7-7 of FIG. 4, with the firing beam in a distal position.

In the present example, a knife member (80) is configured to translate through end effector (40). As best seen in FIGS. 5 and 7A-7B, knife member (80) is secured to the distal end of a firing beam (82), which extends through a portion of shaft assembly (30). As best seen in FIGS. 4 and 6, knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above and as shown in FIGS. 7A-7B, knife member (80) also drives wedge sled (78) distally as knife member (80) translates distally through end effector (40), thereby driving staples (77) through tissue and against anvil (60) into formation. Various features that may be used to drive knife member (80) distally through end effector (40) will be described in greater detail below.

In some versions, end effector (40) includes lockout features that are configured to prevent knife member (80) from advancing distally through end effector (40) when a staple cartridge (70) is not inserted in lower jaw (50). In addition or in the alternative, end effector (40) may include lockout features that are configured to prevent knife member (80) from advancing distally through end effector (40) when a staple cartridge (70) that has already been actuated once (e.g., with all staples (77) deployed therefrom) is inserted in lower jaw (50). By way of example only, such lockout features may be configured in accordance with at least some of the teachings of U.S. Pub. No. 2014/0239041, entitled "Lockout Feature for Movable Cutting Member of Surgical Instrument," published Aug. 28, 2014, now U.S. Pat. No. 9,717,497, issued Aug. 1, 2017, the disclosure of which is incorporated by reference herein; and/or at least some of the teachings of U.S. patent application Ser. No. 14/314,108, entitled "Method of Using Lockout Features for Surgical Stapler Cartridge," filed on Jun. 25, 2014, published as U.S. Patent Pub. No. 2015/0374373 on Dec. 31, 2015, the disclosure of which is incorporated by reference herein. Other suitable forms that lockout features may take will be apparent to those of ordinary skill in the art in view of the teachings herein. Alternatively, end effector (40) may simply omit such lockout features.

C. Exemplary Actuation of Anvil

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. Pub. No. 2014/0239036, entitled "Jaw Closure Feature for End Effector of Surgical Instrument," published Aug. 28, 2014, now U.S. Pat. No. 9,839,421, issued Dec. 12, 2017, the disclosure of which is incorporated by reference herein; and/or in accordance with at least some of the teachings of U.S. patent application Ser. No. 14/314,108, entitled "Jaw Opening Feature for Surgical Stapler," filed on Jun. 25, 2014, published as U.S. Patent Pub. No. 2015/0374373 on Dec. 31, 2015, the disclosure of which is incorporated by reference herein. Exemplary features that may be used to provide longitudinal translation of closure ring (36) relative to end effector (40) will be described in greater detail below.

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein. When closure trigger (24) reaches a fully pivoted state, such that anvil (60) is in a fully closed position relative to lower jaw (50), locking features in handle assembly (20) lock the position of trigger (24) and closure tube (32), thereby locking anvil (60) in a fully closed position relative to lower jaw (50). These locking features are released by actuation of anvil release button (25). Anvil release button (25) is configured and positioned to be actuated by the thumb of the operator hand that grasps pistol grip (22). In other words, the operator may grasp pistol grip (22) with one hand, actuate closure trigger (24) with one or more fingers of the same hand, and then actuate anvil release button (25) with the thumb of the same hand, without ever needing to release the grasp of pistol grip (22) with the same hand. Other suitable features that may be used to actuate anvil (60) will be apparent to those of ordinary skill in the art in view of the teachings herein.

D. Exemplary Actuation of Firing Beam

In the present example, instrument (10) provides motorized control of firing beam (82). In particular, instrument (10) includes motorized components that are configured to drive firing beam (82) distally in response to pivoting of firing trigger (26) toward pistol grip (22). In some versions, a motor (not shown) is contained in pistol grip (22) and receives power from battery pack (28). This motor is coupled with a transmission assembly (not shown) that converts rotary motion of a drive shaft of the motor into linear translation of firing beam (82). In some such versions, firing beam (82) may only be advanced distally when anvil (60) is in a fully closed position relative to lower jaw (50). After firing beam (82) is advanced distally to sever tissue and drive staples (77) as described above with reference to FIGS. 7A-7B, the drive assembly for firing beam (82) may be automatically reversed to drive firing beam (82) proximally back to the retracted position (e.g., back from the position shown in FIG. 7B to the position shown in FIG. 7A). Alternatively, the operator may actuate firing beam reverse switch (27), which may reverse the drive assembly for firing beam (82) in order to retract firing beam (82) to a proximal position. Handle assembly (20) of the present example further includes a bailout feature (21), which is operable to provide a mechanical bailout allowing the operator to manually retract firing beam (82) proximally (e.g., in the event of power loss while firing beam (82) is in a distal position, etc.).

By way of example only, the features that are operable to provide motorized actuation of firing beam (82) may be configured and operable in accordance with at least some of the teachings of U.S. Pat. No. 8,210,411, entitled "Motor-Driven Surgical Instrument," issued Jul. 3, 2012, the disclosure of which is incorporated by reference herein. As another merely illustrative example, the features that are operable to provide motorized actuation of firing beam (82) may be configured and operable in accordance with at least some of the teachings of U.S. Pat. No. 8,453,914, entitled "Motor-Driven Surgical Cutting Instrument with Electric Actuator Directional Control Assembly," issued Jun. 4, 2013, the disclosure of which is incorporated by reference herein. As yet another merely illustrative example, the features that are operable to provide motorized actuation of firing beam (82) may be configured and operable in accordance with at least some of the teachings of U.S. patent application Ser. No. 14/226,142, entitled "Surgical Instrument Comprising a Sensor System," filed Mar. 26, 2014, now U.S. Pat. No. 9,913,642, issued Mar. 13, 2018, the disclosure of which is incorporated by reference herein.

Other suitable components, features, and configurations that may be used to provide motorization of firing beam (82) will be apparent to those of ordinary skill in the art in view of the teachings herein. It should also be understood that some other versions may provide manual driving of firing beam (82), such that a motor may be omitted. By way of example only, firing beam (82) may be manually actuated in accordance with at least some of the teachings of any other reference cited herein.

FIG. 8 shows end effector (40) having been actuated through a single stroke through tissue (90). As shown, cutting edge (84) (obscured in FIG. 8) has cut through tissue (90), while staple drivers (75) have driven two alternating rows of staples (77) through the tissue (90) on each side of the cut line produced by cutting edge (84). Staples (77) are all oriented substantially parallel to the cut line in this example, though it should be understood that staples (77) may be positioned at any suitable orientations. In the present example, end effector (40) is withdrawn from the trocar after the first stroke is complete, the spent staple cartridge (70) is replaced with a new staple cartridge (70), and end effector (40) is then again inserted through the trocar to reach the stapling site for further cutting and stapling. This process may be repeated until the desired amount of cuts and staples (77) have been provided. Anvil (60) may need to be closed to facilitate insertion and withdrawal through the trocar; and anvil (60) may need to be opened to facilitate replacement of staple cartridge (70).

It should be understood that cutting edge (84) may cut tissue substantially contemporaneously with staples (77) being driven through tissue during each actuation stroke. In the present example, cutting edge (84) just slightly lags behind driving of staples (77), such that a staple (47) is driven through the tissue just before cutting edge (84) passes through the same region of tissue, though it should be understood that this order may be reversed or that cutting edge (84) may be directly synchronized with adjacent staples. While FIG. 8 shows end effector (40) being actuated in two layers (92, 94) of tissue (90), it should be understood that end effector (40) may be actuated through a single layer of tissue (90) or more than two layers (92, 94) of tissue. It should also be understood that the formation and positioning of staples (77) adjacent to the cut line produced by cutting edge (84) may substantially seal the tissue at the cut line, thereby reducing or preventing bleeding and/or leaking of other bodily fluids at the cut line. Furthermore, while FIG. 8 shows end effector (40) being actuated in two substantially flat, apposed planar layers (92, 94) of tissue, it should be understood that end effector (40) may also be actuated across a tubular structure such as a blood vessel, a section of the gastrointestinal tract, etc. FIG. 8 should therefore not be viewed as demonstrating any limitation on the contemplated uses for end effector (40). Various suitable settings and procedures in which instrument (10) may be used will be apparent to those of ordinary skill in the art in view of the teachings herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Alternative Staple Drivers

End effector (40) may be structured to provide a predefined gap separating the surface of cartridge deck (73) and the corresponding surface of anvil (60) when anvil (60) is in a closed position. In some instances, cutting and stapling tissue may be challenging if the thickness of the target tissue differs from this predefined gap distance. For example, if the target tissue is significantly thicker than the gap, an operator may have trouble firing the instrument to effectively cut and staple the tissue. On the other hand, if the target tissue is thinner than the gap between the cartridge deck and the anvil, it may be difficult to maintain the position of the target tissue between anvil (60) and deck (73). Particularly, during firing, as knife member (80) advances against the tissue, the tissue may shift position within the jaws of the instrument, thereby making it challenging to effectively cut the target tissue. In some instances, staples (77) are driven through regions of tissue before knife member (80) reaches the same regions of tissue, such that the legs of staples (77) are disposed in the tissue before that region of tissue is severed. In such instances where the tissue is so thin that the tissue is not being held in place due to compression between anvil (60) and deck (73), knife member (80) may plow the tissue rather than cutting it cleanly, which may result in staples (77) tearing through the tissue through a cheese wire effect.

In view of the foregoing, it may be desirable to provide one or more features in end effector (40) that compress relatively thin tissue to thereby secure the tissue as knife member (80) is actuated. Such compression of tissue may prevent undesirable movement of tissue that might otherwise occur when the tissue is positioned between a closed anvil (60) and deck (73). Several examples of tissue compression features are described in greater detail below, while other examples will be apparent to those of ordinary skill in the art in view of the teachings herein.

FIGS. 9A-12 show exemplary alternative staple drivers (175, 275, 375, 475), each of which may be readily incorporated into staple cartridge (70) in place of staple driver (75). Staple drivers (175, 275, 375, 475) are configured to operate in a substantially similar manner as staple driver (75). That is, staple drivers (175, 275, 375, 475) are configured to be incorporated into a staple cartridge of a surgical instrument, such as staple cartridge (70) of surgical instrument (10). For example, staple drivers (175, 275, 375, 475) are configured to be received, along with a staple (77), in a plurality of staple pockets (74) of a staple cartridge (70) of a lower jaw (50), and are configured to be driven upwardly by wedge sled (78) in response to longitudinal advancement of firing beam (82). Therefore, staple drivers (175, 275, 375, 475) are configured to drive staples (77) upwardly through staple pockets (74) and into engagement with anvil (60) in the same manner as described with respect to staple drivers (75). However, staple drivers (175, 275, 375, 475) of the present example further include compressible features that are configured to hold portions of tissue in place during stapling and severing of tissue.

FIGS. 9A-9B and 13A-14C show staple driver (175). It will be appreciated by persons skilled in the art that in some examples, a staple cartridge (70) may include a plurality of staple drivers (175), according to the number of staples (77) and staple pockets (74) for example. However, in some other examples, a staple cartridge (70) may include any combination or number of staple drivers (75, 175, 275, 375, 475) or other suitable staple drivers, as will be apparent to persons skilled in the art in view of the teachings herein. FIGS. 13A-14C show a plurality of staple drivers (175) incorporated into an exemplary alternative end effector (140). As discussed in further detail below, end effector (140) is configured to be incorporated into a surgical instrument, such as surgical instrument (10), and is configured to operate substantially similar to end effector (40).

As shown, staple driver (175) includes a body (176) and a support portion (178) that is configured to support a crown portion (77a) (FIGS. 14A-14C) of a staple (77). Staple driver (175) further comprises a compressible feature (180) that is configured to hold portions of tissue in place during stapling and severing of tissue, as discussed in further detail below. In the example shown, compressible feature (180) comprises a pair of arcuate members (182a, 182b) on opposing sides of body (176). As shown, each arcuate member extends substantially from one end of staple driver (175) to another end of staple driver (175). Staple driver (175) includes a set of openings (184) between arcuate members (182a, 182b) that, as discussed in further detail below, allow arcuate members (182a, 182b) to deflect in a downward direction toward body (176). Arcuate members (182a, 182b) are configured and positioned such that crown portion (77a) may freely pass between arcuate members (182a, 182b) to reach and rest against support portion (178) as staple (77) is seated on staple driver (175).

In the example shown, arcuate members (182a, 182b) each comprise an elastomer, polymer, and/or other suitable material. In the example shown, arcuate members (182a, 182b) are co-molded with staple driver (175) such that arcuate members (182a, 182b) are integral with body (176) of staple driver (175). In some examples, arcuate members (182a, 182b) may be overmolded onto body (176) of staple driver (175). Alternatively, arcuate members (182a, 182b) may be fixed to body (176) of staple driver (175) by other suitable methods that will be apparent to persons skilled in the art in view of the teachings herein. Arcuate members (182a, 182b) are configured to be rigid enough to urge tissue toward and against anvil (60) once a staple (77) associated with staple driver (175) has been partially fired; but compressible enough so as not to prevent the associated staple (77) from being fired completely, as will be discussed in further detail below. Other suitable configurations of compressible feature (180) will be apparent to persons skilled in the art in view of the teachings herein.

Figure 10:
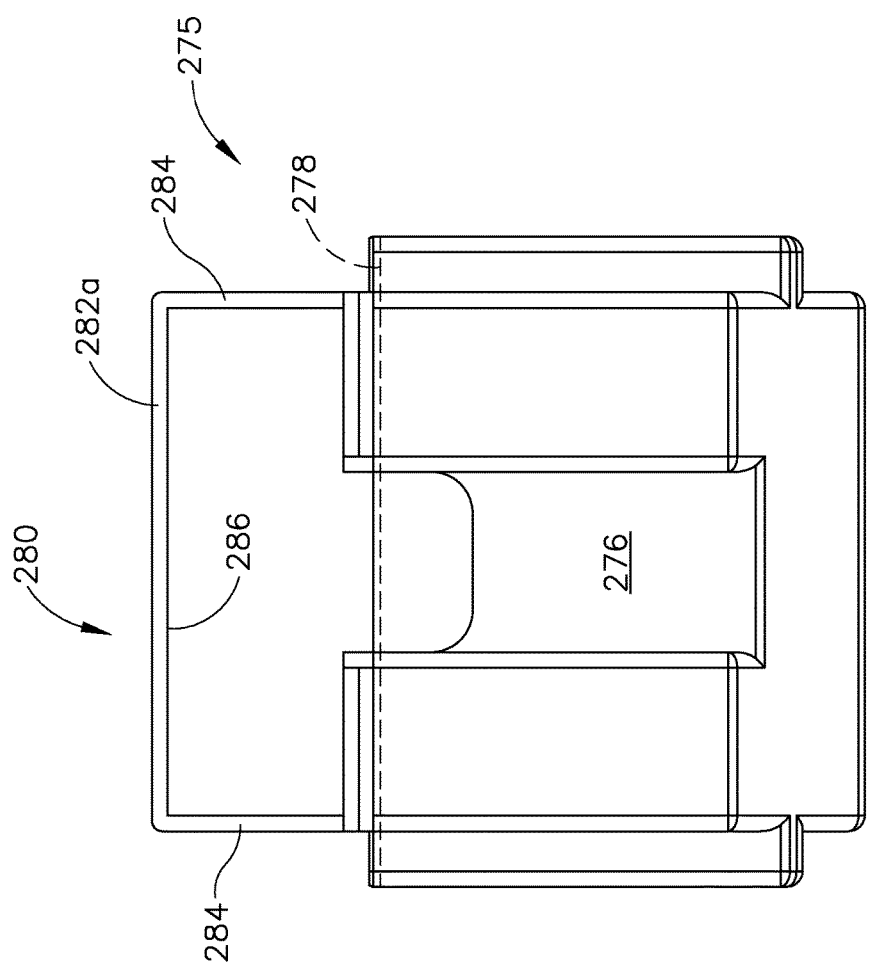
FIG. 10 depicts a side elevational view of another exemplary alternative staple driver that may be incorporated into a staple cartridge used in the end effector of FIG. 3.

FIG. 10 shows another exemplary alternative staple driver (275). It will be appreciated by persons skilled in the art that in some examples, a staple cartridge (70) may include a plurality of staple drivers (275), according to the number of staples (77) and staple pockets (74) for example. However, in some other examples, a staple cartridge (70) may include any combination of staple drivers (75, 175, 275, 375, 475) or suitable other suitable staple drivers, as will be apparent to persons skilled in the art in view of the teachings herein.

Figure 9A:
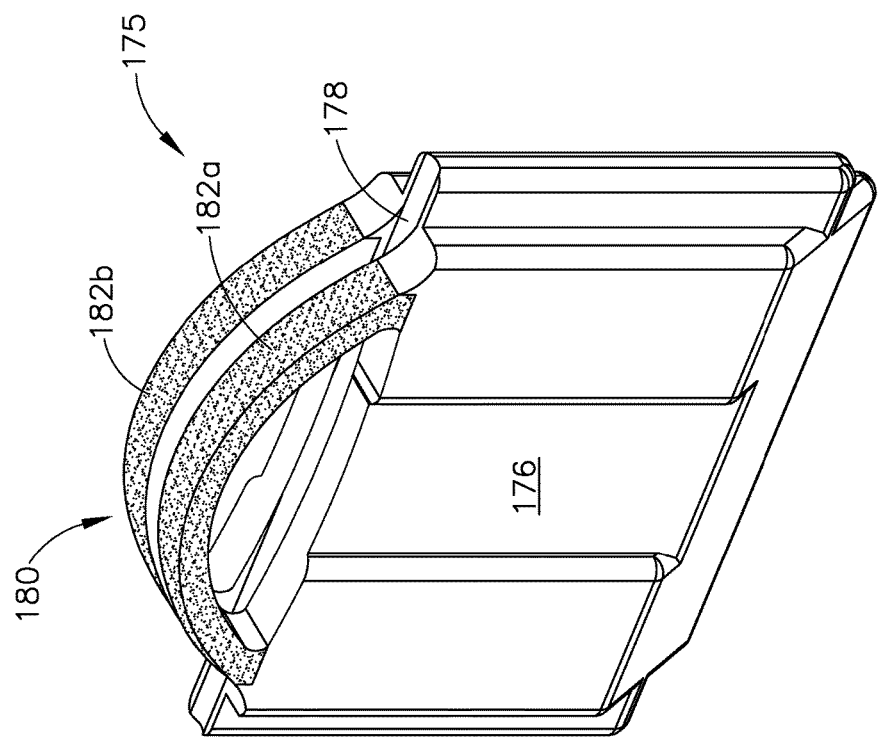
FIG. 9A depicts a perspective view of an exemplary alternative staple driver that may be incorporated into a staple cartridge used in the end effector of FIG. 3.
Figure 9B:
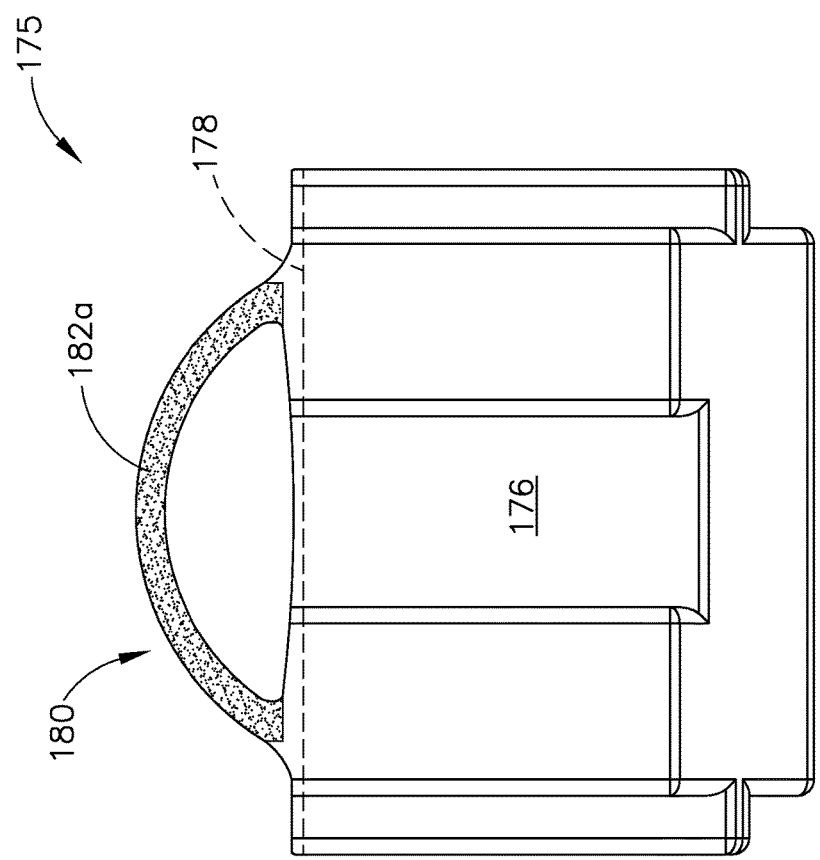
FIG. 9B depicts a side elevational view of the staple driver of FIG. 9A.

It will be appreciated that FIG. 10 shows a side view of staple driver (275) (similar to the side view of staple driver (175) shown in FIG. 9B). As shown, staple driver (275) includes a body (276) and is substantially similar to staple driver (175), except that staple driver (275) includes a differently shaped compressible feature (280). In particular, compressible feature (280) of this example comprises opposing bridge members (282a). While only one bridge member (282a) is shown, it will be appreciated that staple driver (275) includes a substantially identical second bridge member opposing bridge member (282a), with the two bridge members (282a) being configured and positioned such that crown portion (77a) may freely pass between bridge members (282a) to reach and rest against a support portion (278) as staple (77) is seated on staple driver (275). As shown in the present example, bridge member (282a) includes a pair of opposing vertical members (284) and a horizontal member (286) extending therebetween. Staple driver (275) further includes support portion (278) (shown in hidden lines) configured to support a crown portion (77a) (FIGS. 14A-14C) of a staple (77).

In the example shown, bridge members (282a) each comprise an elastomer, polymer, and/or other suitable material as will be apparent to persons skilled in the art in view of the teachings herein. In the example shown, bridge members (282a, not shown) are co-molded with staple driver (275) such that bridge members (282a, not shown) are integral with body (276) of staple driver (275). In some examples, bridge members (282a) may be overmolded onto body (276) of staple driver (275). Alternatively, bridge members (282a) may be fixed to body (276) of staple driver (275) by other suitable methods that will be apparent to persons skilled in the art in view of the teachings herein. Bridge members (282a) are configured to be rigid enough to urge tissue toward anvil (60) once a staple (77) associated with staple driver (275) has been partially fired; but compressible enough so as not to prevent the associated staple (77) from being fired completely, as will be discussed in further detail below. Other suitable configurations of compressible feature (280) will be apparent to persons skilled in the art in view of the teachings herein.

Figure 11:
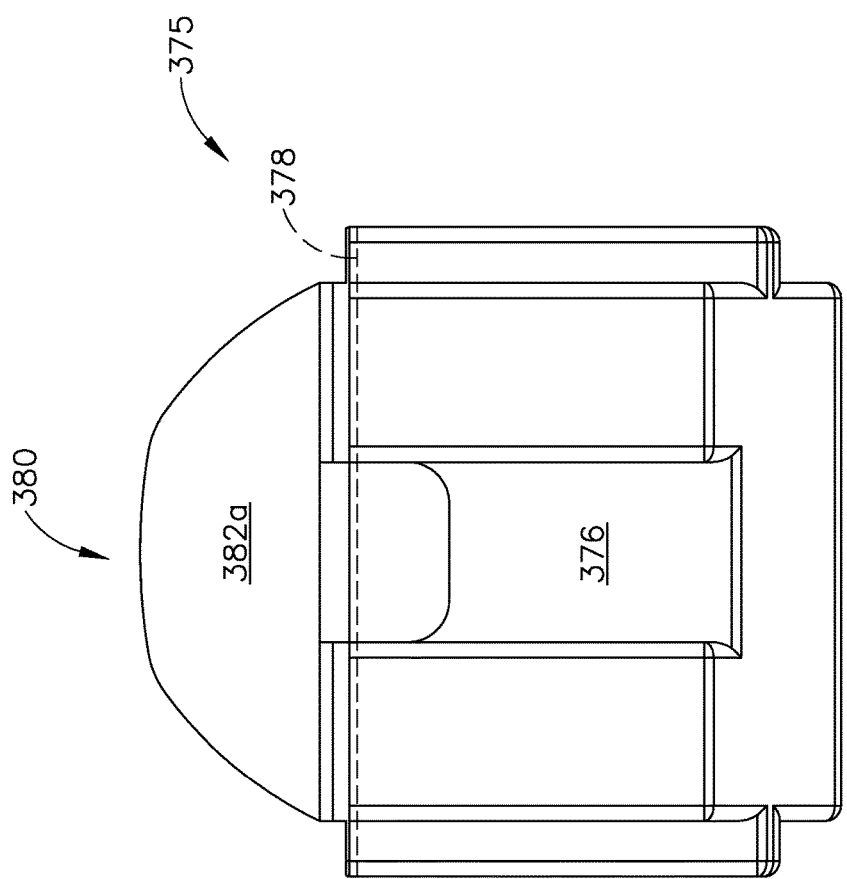
FIG. 11 depicts a side elevational view of another exemplary alternative staple driver that may be incorporated into a staple cartridge used in the end effector of FIG. 3.

FIG. 11 shows another exemplary alternative staple driver (375). It will be appreciated by persons skilled in the art that, in some examples, a staple cartridge (70) may include a plurality of staple drivers (275), according to the number of staples (77) and staple pockets (74) for example. However, in some other examples, a staple cartridge (70) may include any combination of staple drivers (75, 175, 275, 375, 475) or suitable other suitable staple drivers, as will be apparent to persons skilled in the art in view of the teachings herein.

It will be appreciated that FIG. 11 shows a side view of staple driver (375) (similar to the side views of staple driver (175, 275) shown in FIGS. 9B and 10). As shown, staple driver (375) includes a body (376) and is substantially similar to staple driver (175), except that staple driver (375) includes a differently shaped compressible feature (380). In particular, compressible feature (380) of this example comprises opposing arcuate members (382a). While only one arcuate member (382a) is shown, it will be appreciated that staple driver (375) includes a substantially identical arcuate member opposing arcuate member (382a), with the two arcuate members (382a) being configured and positioned such that crown portion (77a) may freely pass between arcuate members (382a) to reach and rest against a support portion (378) as staple (77) is seated on staple driver (375). As shown, compressible feature (380) is shaped similarly to compressible feature (180), except that arcuate members (382a) are solid such that they do not include an opening like opening (184). Staple driver (375) further includes support portion (378) (shown in hidden lines) configured to support a crown portion (77a) (FIGS. 14A-14C) of a staple (77).

In the example shown, arcuate members (382a) each comprise an elastomer, polymer, and/or other suitable material as will be apparent to persons skilled in the art in view of the teachings herein. In the example shown, arcuate members (382a) are co-molded with staple driver (375) such that arcuate members (382a) are integral with body (376) of staple driver (375). In some examples, arcuate members (382a) may be overmolded onto body (376) of staple driver (375). Alternatively, arcuate members (382a) may be fixed to body (376) of staple driver (375) by other suitable methods that will be apparent to persons skilled in the art in view of the teachings herein. Arcuate members (382a) are configured to be rigid enough to urge tissue toward anvil (60) once a staple (77) associated with staple driver (375) has been partially fired; but compressible enough so as not to prevent the associated staple (77) from being fired completely, as will be discussed in further detail below. Other suitable configurations of compressible feature (380) will be apparent to persons skilled in the art in view of the teachings herein.

FIG. 12 shows another exemplary alternative staple driver (475). It will be appreciated by persons skilled in the art that, in some examples, a staple cartridge (70) may include a plurality of staple drivers (475), according to the number of staples (77) and staple pockets (74) for example. However, in some other examples, a staple cartridge (70) may include any combination of staple drivers (75, 175, 275, 375, 475) or suitable other staple drivers, as will be apparent to persons skilled in the art in view of the teachings herein.

It will be appreciated that FIG. 12 shows a side view of staple driver (475) (similar to the side views of staple driver (175, 275, 375) shown in FIGS. 9B, 10, and 11). As shown, staple driver (475) includes a body (476) and is substantially similar to staple driver (175), except that staple driver (475) includes a differently shaped compressible feature (480). In particular, compressible feature (480) of this example comprises opposing sets of compressible fingers (482). While only one set of four compressible fingers (482a) is shown, it will be appreciated that staple driver (475) includes a substantially identical set of compressible fingers (not shown) opposing compressible fingers (482a), with both opposing sets of compressible fingers (482a) configured and positioned such that crown portion (77a) may freely pass between the opposing sets of fingers (482a) to reach and rest against a support portion (478) as staple (77) is seated on staple driver (475). Staple driver (475) further includes support portion (478) (shown in hidden lines) configured to support a crown portion (77a) (FIGS. 14A-14C) of a staple (77).

In the example shown, compressible fingers (482a) each comprise an elastomer, polymer, or other suitable material as will be apparent to persons skilled in the art in view of the teachings herein. In the example shown, compressible fingers (482a, not shown) are co-molded with staple driver (475) such that compressible fingers (482a, not shown) are integral with body (476) of staple driver (475). In some examples, compressible fingers (482a) may be overmolded onto body (476) of staple driver (475). Alternatively, compressible fingers (482a) may be fixed to body (476) of staple driver (475) by other suitable methods that will be apparent to persons skilled in the art in view of the teachings herein. Compressible fingers (482a, not shown) are configured to be rigid enough to urge tissue toward anvil (60) once a staple (77) associated with staple driver (475) has been partially fired, but compressible such that they compress and do not hamper the associated staple (77) from being fired, as will be discussed in further detail below. Suitable other configurations of compressible feature (480) will be apparent to persons skilled in the art in view of the teachings herein.

As discussed above, FIGS. 13A-14C show an exemplary alternative end effector (140) that includes a version of staple cartridge (70) incorporating a plurality of staple drivers (175). As also discussed above, end effector (140) may be readily incorporated into surgical instrument (10) in place of end effector (40). As shown, two layers (92, 94) of tissue (90) are positioned between anvil (60) and lower jaw (50). By way of example only, the two layers (92, 94) may be provided by opposing walls of a single anatomical structure, such as a large vessel, a section of the gastrointestinal tract, a section of a lung or other organ, and/or any other suitable anatomical structure.

Figure 13A:
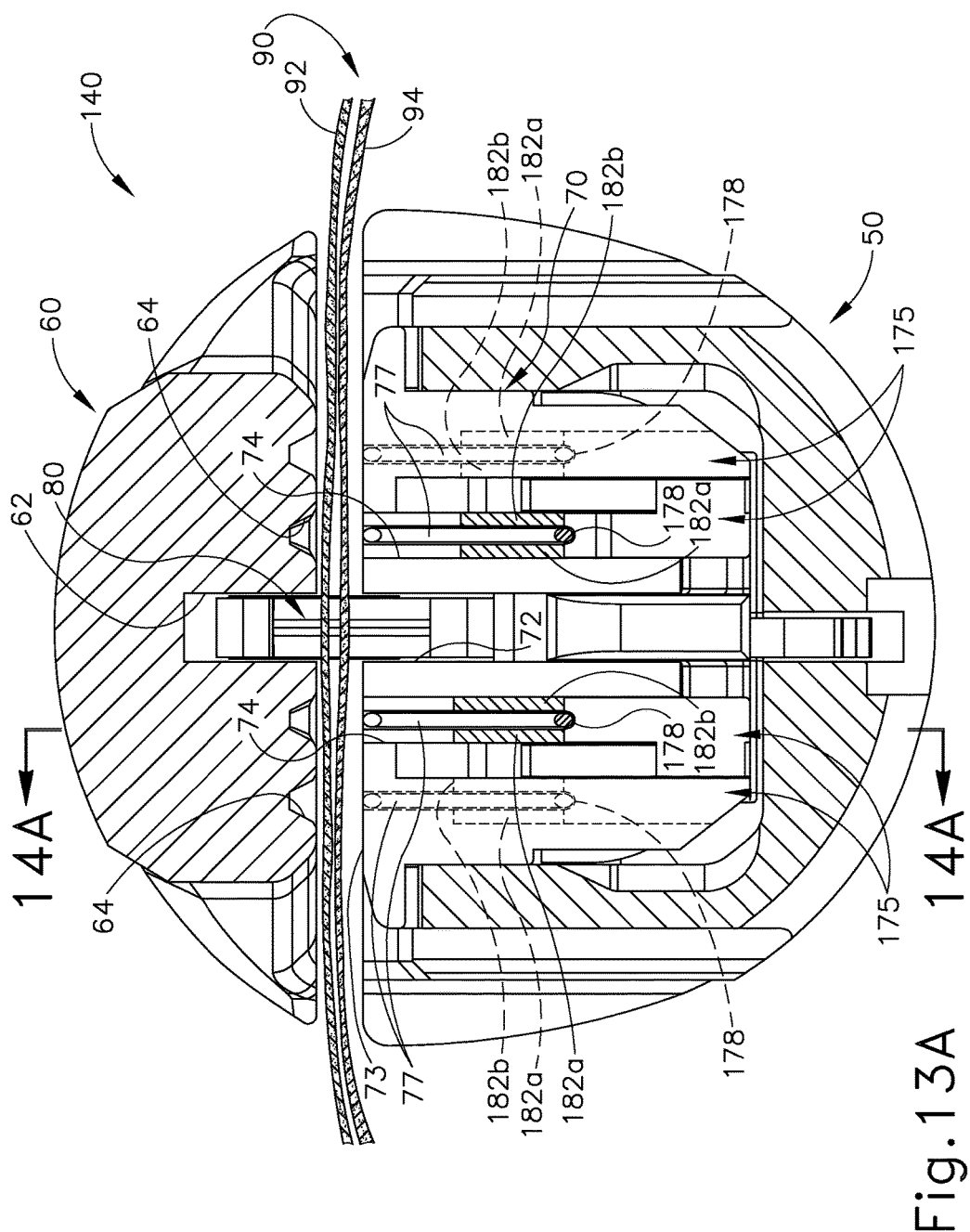
FIG. 13A depicts a cross-sectional end view of an exemplary alternative end effector incorporating the staple driver of FIG. 9A in multiple form, with a firing beam in a proximal position and staples being in an unfired position.
Figure 13B:
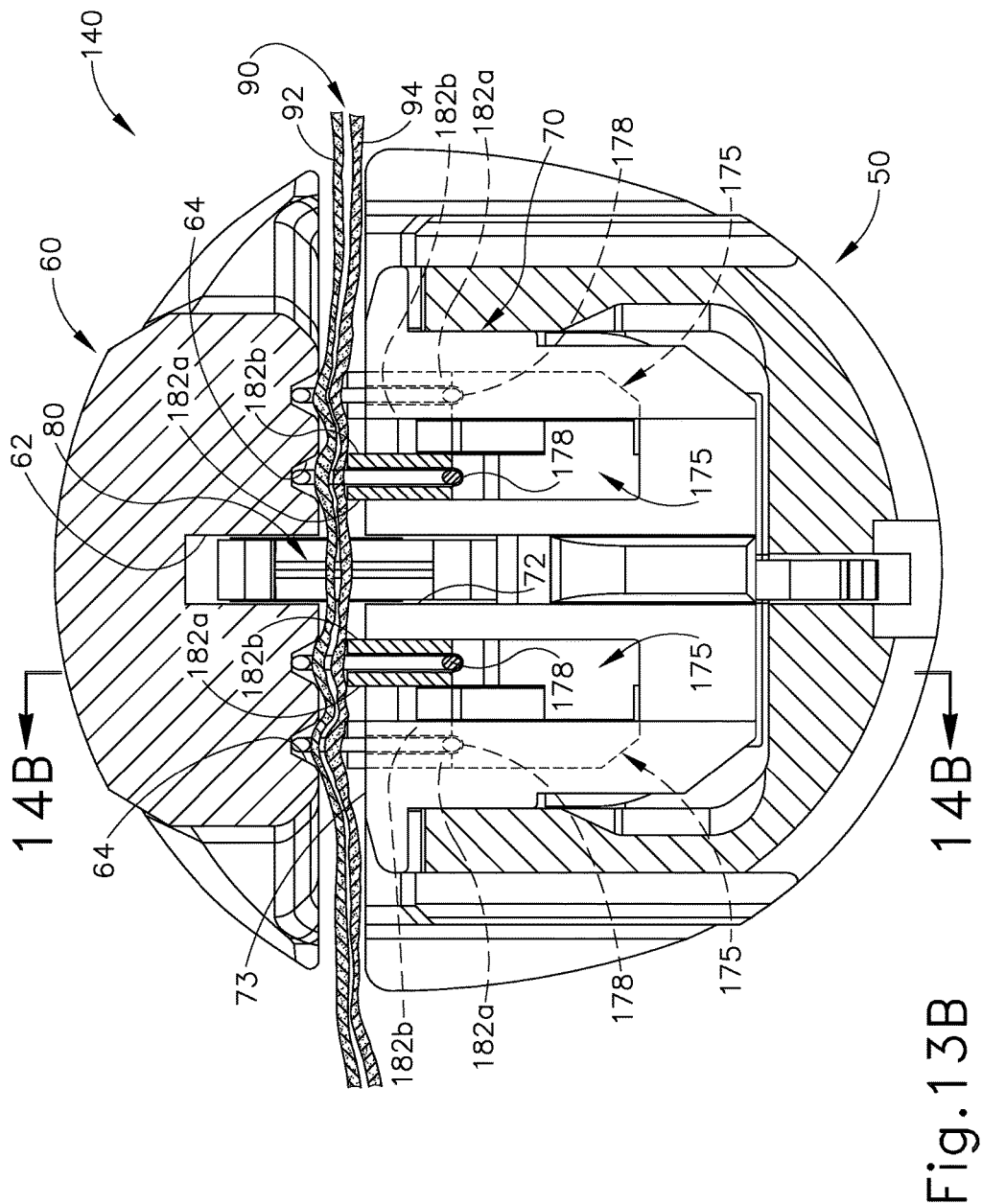
FIG. 13B depicts a cross-sectional end view of the end effector of FIG. 13A, with the firing beam in an intermediate position and staples in an intermediate position.
Figure 13C:
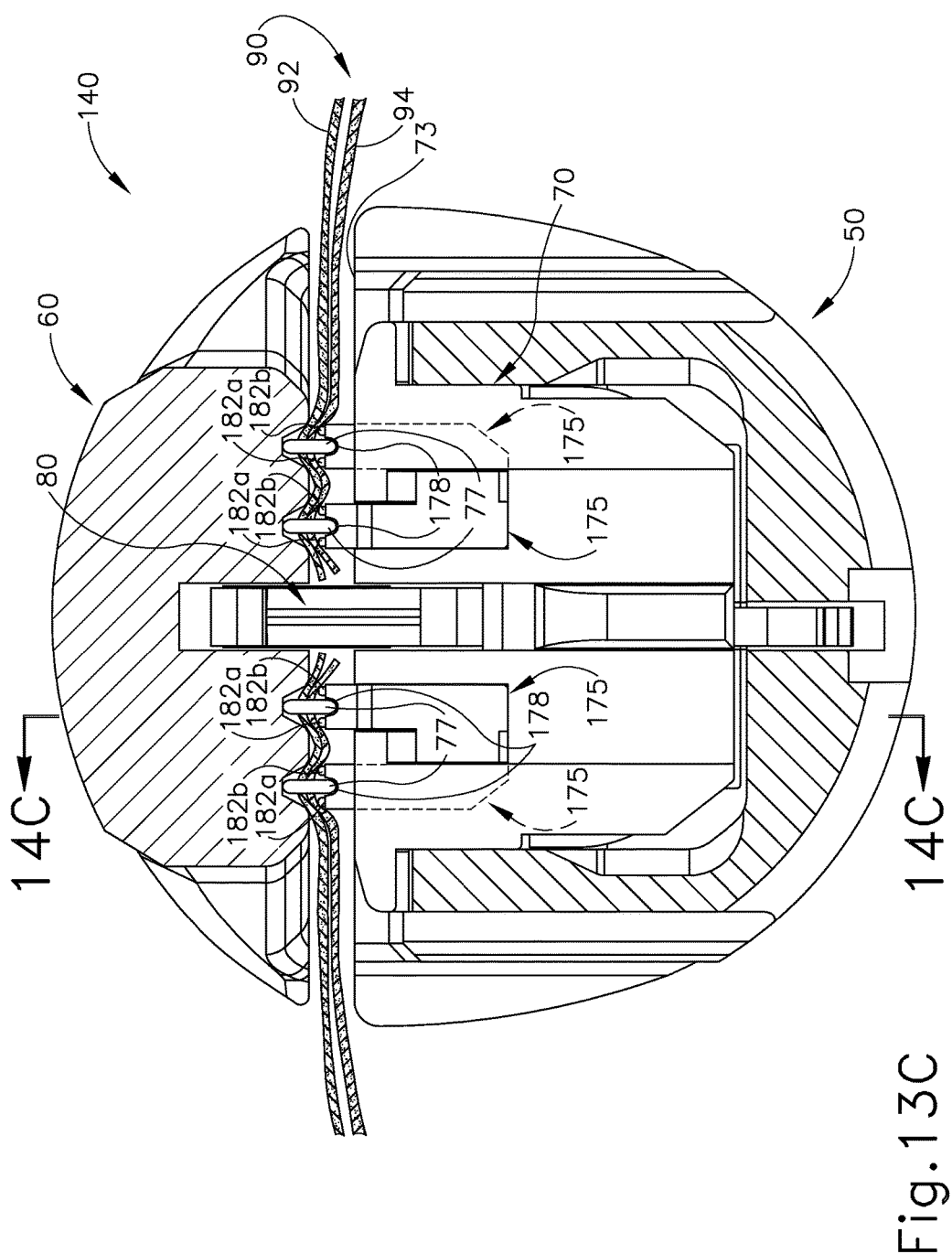
FIG. 13C depicts a cross-sectional end view of the end effector of FIG. 13A, with the firing beam in a distal position and staples in a fired position.
Figure 14A:
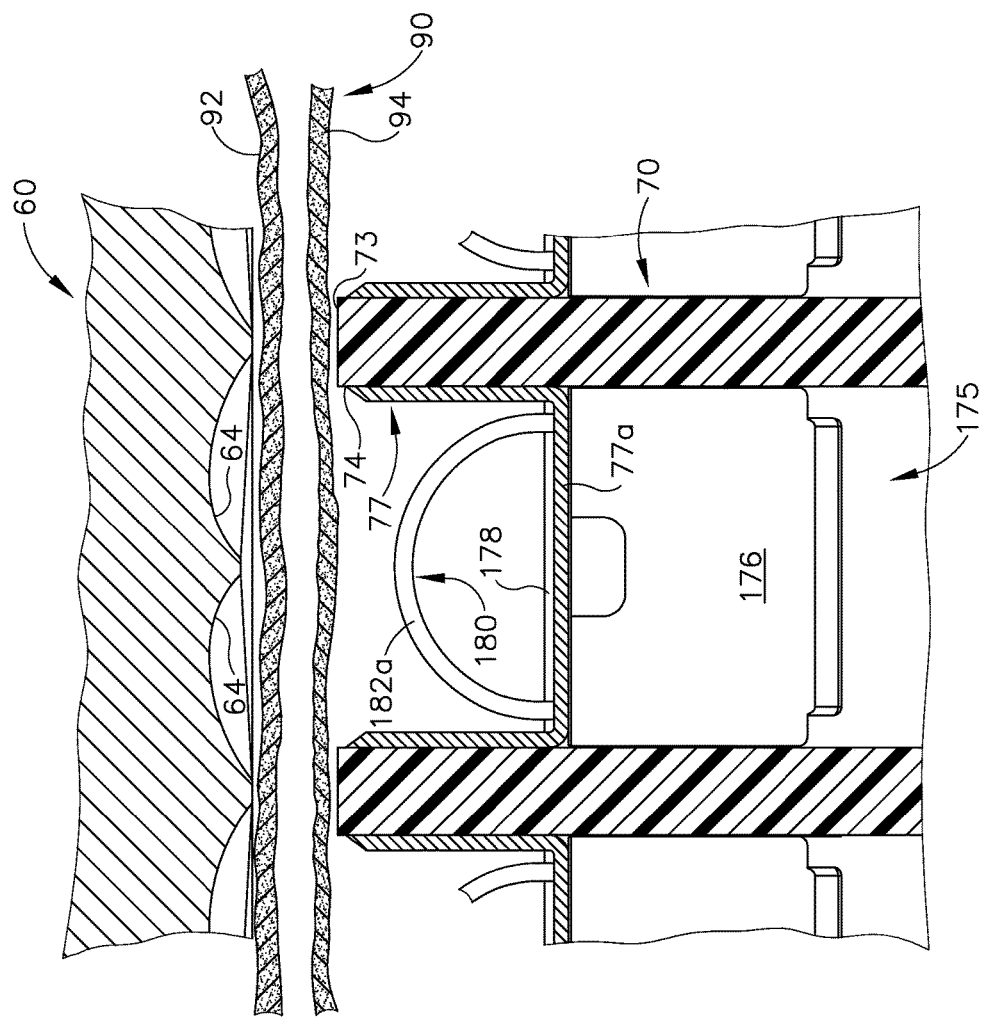
FIG. 14A depicts a partial, cross-sectional side view of the end effector of FIG. 13A, taken along line 14A-14A of FIG. 13A, showing a staple in the unfired position.
Figure 14B:
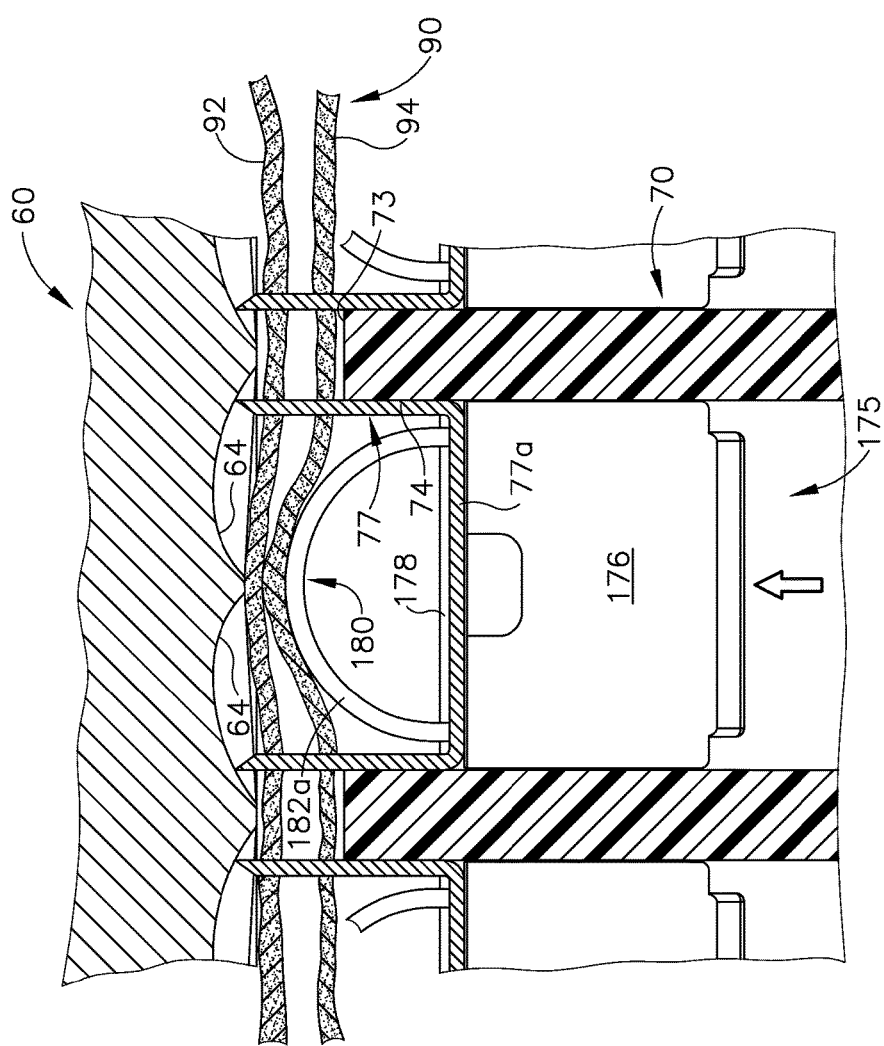
FIG. 14B depicts a partial, cross-sectional side view of the end effector of FIG. 13B, taken along line 14B-14B of FIG. 13B, showing the staple in a first intermediate position.

In the example shown, the combined thickness of the layers (92, 94) of tissue (90) in the region between cartridge deck (73) and anvil (60) is less than the predefined gap distance between anvil (60) and cartridge deck (73) with anvil (60) in the closed position. FIGS. 13A and 14A show staples (77) prior to being fired; FIGS. 13B and 14B show staples (77) in a first partially fired state; and FIGS. 13C and 14C show staples (77) in a second partially fired state. In FIGS. 13A and 14A, firing beam (82) has not yet advanced to a position whereby wedge sled (78) is in contact with staple drivers (175). Thus, staple drivers (175) are in a retracted position within staple pockets (74). As shown, when staple drivers are in the retracted position, compressible member (180) lies below cartridge deck (73) and thus does not yet contact tissue (90). At this stage, even though anvil (60) is in a closed position, tissue (90) may still move between anvil (60) and cartridge deck (73) since the combined thickness of the layers (92, 94) of tissue (90) in the region between cartridge deck (73) and anvil (60) is less than the predefined gap distance between anvil (60) and cartridge deck (73) with anvil (60) in the closed position.

As firing beam (82) advances longitudinally, and as shown in FIGS. 13B and 14B, wedge sled (78) advances into contact with staple drivers (175), driving staple drivers (175) and staples (77) upwardly toward anvil (60). Eventually, compressible feature (180) extends above cartridge deck (73) such that compressible members (182a, 182b) contact tissue (90), and compress tissue (90) against anvil (60) as wedge sled (78) drives staple drivers (175) further upwardly. As discussed above, compressible feature (180) is configured to be rigid enough to urge the tissue (90) toward anvil (60) and compress the tissue (90) against anvil (60). It should be understood that, in the longitudinal region of cartridge (70) where compressible feature (180) is compressing tissue (90) against anvil (60), knife member (80) has not yet severed the corresponding region of tissue (90). In other words, compressible features (180) will compress the tissue (90) against anvil (60) before knife member (80) reaches that particular region of tissue (90).

As wedge sled (78) continues to move longitudinally, staple drivers (175) eventually reach a position where staples (77) are fully fired. In other words, staples (77) are fully driven into staple forming pockets (64) to deform into a B-shape as understood in the art, with arcuate members (182a, 182b) continuing to urge tissue (90) against anvil (60). As discussed above and shown in FIGS. 13C and 14C, arcuate members (182a, 182b) are compressible a sufficient amount so as not to hamper the full firing of the associated staple (77). As shown, as firing beam (82) advances further longitudinally, knife member (80) severs tissue substantially contemporaneously with the completion of firing of the staples (77), as discussed in detail above with respect to end effector (40). This process may be repeated until the desired amount of cuts and staples (77) have been provided. In some versions, the state shown in FIG. 14C constitutes a fully fired state. In some other versions, the state shown in FIG. 14C constitutes a second partially fired state. In such versions, the depicted staple (77) may be further deformed to continue forming a "B" shape as arcuate members (182a, 182b) continue to urge tissue (90) against anvil (60).

It should be understood from the foregoing that compressible features (180) will prevent the tissue (90) from sliding between deck (73) and anvil (60) as knife member (80) is being driven through the tissue. Compressible features (180) thus cooperate with anvil (60) to securely hold the tissue (90) for cutting by knife member (80), even though the thickness of tissue (90) is smaller than the predefined gap formed between deck (73) and closed anvil (60). It should also be understood that compressible features (180) provide pressure against tissue (90) in a highly localized fashion, right at the regions of tissue (90) where staples (77) will be driven through tissue (90). This localized application of compression may prevent tissue (90) from sliding relative to staples (77) as staples (77) are being driven through tissue (90), which may further prevent staples (77) from unnecessarily tearing through the tissue (90) by laterally impinging on the tissue (90) in a cheese wire effect as staples (77) are being driven through tissue (90).

In the present example, and as shown in FIGS. 13A and 14A, compressible features (180) are sized and configured such that compressible features (180) are recessed below the surface of deck (73) when staple drivers (175) are in a non-actuated state. In some other versions, compressible features (180) are sized and configured such that at least a portion of compressible features (180) protrude above the surface of deck (73) when staple drivers (175) are in a non-actuated state. In such versions, end effector (140) may be used as a tissue grasper by selectively opening and closing anvil (60), even with thin tissue structures, without necessarily firing knife member (80). Other suitable ways in which staple drivers (175) may be varied and used will be apparent to those of ordinary skill in the art in view of the teachings herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body; (b) a shaft assembly extending distally from the body; (c) an end effector, wherein the end effector comprises: (i) an anvil, and (ii) a lower jaw, wherein the anvil is pivotable toward the lower jaw to clamp tissue; and (d) a staple cartridge coupled with the lower jaw, wherein the staple cartridge comprises: (i) a deck facing the anvil, (ii) a plurality of staples positioned in a plurality of staple openings formed through the deck, and (iii) a plurality of staple drivers configured to drive the staples out of the staple openings, wherein each staple driver of the plurality of staple drivers comprises a staple driver body, wherein at least a portion of the staple drivers further comprise a compressible feature extending from the staple driver body toward the anvil.

Example 2

The apparatus of Example 1, wherein each compressible feature comprises an arcuate member.

Example 3

The apparatus of any one or more of Examples 1 through 2, wherein each staple driver body has a first end and a second end, wherein the corresponding arcuate member extends from the first end to the second end.

Example 4

The apparatus of Example 3, wherein each staple driver further defines a gap under the corresponding arcuate member, wherein the gap is configured to accommodate deformation of the arcuate member.

Example 5

The apparatus of any one or more of Examples 1 through 4, wherein each staple driver further comprises a staple support portion, wherein each compressible feature comprises opposing compressible members positioned on each side of the corresponding staple support feature.

Example 6

The apparatus of any one or more of Examples 1 through 5, wherein the compressible features each comprise an elastomeric material.

Example 7

The apparatus of any one or more of Examples 1 through 6, wherein the compressible features are configured to deform in response to compression of tissue by the compressible features against the anvil.

Example 8

The apparatus of any one or more of Examples 1 through 7, wherein each compressible feature is configured to transition from an unfired position to a fired position, wherein each compressible feature is configured to protrude past the anvil in the fired position, wherein the fired position is associated with the corresponding staple driver body driving an associated staple against the anvil.

Example 9

The apparatus of Example 8, wherein each compressible feature is configured to be recessed relative to the deck in the unfired position, wherein the fired position is associated with the associated staple also being recessed relative to the deck.

Example 10

The apparatus of any one or more of Examples 1 through 9, further comprising a firing bar configured to move through the end effector, wherein the firing bar is configured to drive the staple drivers toward the anvil to move the staples toward a fired position.

Example 11

The apparatus of Example 10, wherein firing bar is further configured to sever tissue as the firing bar drives the staple drivers toward the anvil.

Example 12

The apparatus of Example 11, wherein the compressible features are configured to compress tissue against the anvil as the firing bar severs the tissue.

Example 13

The apparatus of any one or more of Examples 1 through 12, wherein each of the compressible features comprises a pair of members extending upwardly from the staple driver body.

Example 14

The apparatus of Example 13, wherein the pair of members are configured and positioned to receive a portion of a corresponding staple of the plurality of staples between the members of the pair of members.

Example 15

The apparatus of any one or more of Examples 1 through 14, wherein each compressible member comprises a pair of legs and a bridge extending between the pair of legs.

Example 16

The apparatus of any one or more of Examples 1 through 15, wherein each compressible member comprises a set of fingers.

Example 17

A staple cartridge for use with an end effector of a surgical stapler, the staple cartridge comprising: (a) a cartridge body, wherein the cartridge body includes a cartridge deck, wherein the cartridge body further defines a plurality of staple openings passing through the cartridge deck; (b) a plurality of staples associated with the plurality of staple openings; (c) a plurality of staple drivers associated with the plurality of staple openings and the plurality of staples, wherein the staple drivers are configured to move toward the cartridge deck to drive the staples out of the staple openings; and (d) a plurality of compressible features associated with at least some of the plurality of staple drivers, wherein the compressible features are movable with the associated staple drivers.

Example 18

The staple cartridge of Example 17, wherein the compressible features are configured to be driven through the staple openings and compress tissue against an anvil as the staples are driven through the tissue and into the anvil.

Example 19

A method of using a surgical instrument, wherein the surgical instrument comprises: (a) an end effector, wherein the end effector comprises: (i) an anvil, and (ii) a lower jaw, wherein the anvil is configured to move toward and away from the lower jaw, (iii) a staple cartridge disposed in the lower jaw, wherein the staple cartridge comprises: (A) a plurality of staples, and (B) a plurality of staple drivers, each staple driver being associated with a corresponding staple of the plurality of staples, wherein each staple driver includes an integral compressible feature; and (b) a firing member configured to advance through the end effector to drive the staple drivers toward the anvil, the method comprising: (a) positioning tissue between the anvil and the lower jaw; (b) moving the anvil toward the jaw to place the anvil a closed position; and (c) advancing the firing member through the end effector, wherein advancement of the firing member moves the staples toward the anvil, wherein advancement of the firing member further drives the compressible feature of each staple driver into contact with a portion of the tissue, wherein the compressible feature compresses the corresponding portion of tissue against the anvil.

Example 20

The method of Example 19, wherein the compressible feature of each staple driver deforms as the compressible feature compresses the corresponding portion of tissue against the anvil.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVNCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, now U.S. Pat. No. 8,844,789, issued Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, now U.S. Pat. No. 8,820,605, issued Sep. 2, 2014, the disclosure of which is incorporated by reference herein; U.S. Pub. No. 2012/0132450, entitled "Shiftable Drive Interface for Robotically-Controlled Surgical Tool," published May 31, 2012, now U.S. Pat. No. 8,616,431, issued Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, now U.S. Pat. No.

8,573,461, issued Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, now U.S. Pat. No. 8,602,288, issued Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, now U.S. Pat. No. 9,301,759, issued Apr. 5, 2016, the disclosure of which is incorporated by reference herein; U.S. Pub. No. 2012/0203247, entitled "Robotically-Controlled Surgical End Effector System," published Aug. 9, 2012, now U.S. Pat. No. 8,783,541, issued Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, now U.S. Pat. No. 8,479,969, issued Jul. 9, 2013; U.S. Pub. No. 2012/0138660, entitled "Robotically-Controlled Cable-Based Surgical End Effectors," published Jun. 7, 2012, now U.S. Pat. No. 8,800,838, issued Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, now U.S. Pat. No. 8,573,465, issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a body;
   (b) a shaft assembly extending distally from the body;
   (c) an end effector, wherein the end effector comprises:
      (i) an anvil, and
      (ii) a lower jaw, wherein the anvil is pivotable toward the lower jaw to clamp tissue; and
   (d) a staple cartridge coupled with the lower jaw, wherein the staple cartridge comprises:
      (i) a deck facing the anvil,
      (ii) a plurality of staples positioned in a plurality of staple openings formed through the deck, and
      (iii) a plurality of staple drivers configured to drive the staples out of the staple openings, wherein each staple driver of the plurality of staple drivers comprises:
         (A) a staple driver body including a support portion configured to support a staple of the plurality of staples, and
         (B) at least first and second compressible features extending from the staple driver body toward the anvil, wherein each of the first and second compressible features is positioned and configured to protrude past the deck and directly contact tissue and thereby compress the contacted tissue against the anvil when the staple drivers are driven to a deployed position, wherein the staple of the plurality of staples is configured to be laterally interposed between the first and second compressible features, wherein the first compressible feature is independently compressible relative to the second compressible feature.

2. The apparatus of claim 1, wherein each compressible feature comprises an arcuate member.

3. The apparatus of claim 2, wherein each staple driver body has a first end and a second end, wherein the corresponding arcuate member extends from the first end to the second end.

4. The apparatus of claim 2, wherein each arcuate member defines a gap disposed between a top surface of the staple driver body and a bottom surface of the corresponding arcuate member, wherein the gap is configured to accommodate deformation of the arcuate member by decreasing in size as the arcuate member compresses.

5. The apparatus of claim 1, wherein the compressible features each comprise an elastomeric material.

6. The apparatus of claim 1, wherein the compressible features are configured to deform in response to compression of tissue by the compressible features against the anvil.

7. The apparatus of claim 1, wherein each compressible feature is configured to transition from an unfired position to a fired position, wherein each compressible feature is configured to protrude past the anvil in the fired position, wherein the fired position is associated with the corresponding staple driver body driving an associated staple against the anvil.

8. The apparatus of claim 7, wherein each compressible feature is configured to be recessed relative to the deck in the unfired position, wherein the fired position is associated with the associated staple also being recessed relative to the deck.

9. The apparatus of claim 1, further comprising a firing bar configured to move through the end effector, wherein the firing bar is configured to drive the staple drivers toward the anvil to move the staples toward a fired position.

10. The apparatus of claim 9, wherein firing bar is further configured to sever tissue as the firing bar drives the staple drivers toward the anvil.

11. The apparatus of claim 10, wherein the compressible features are configured to compress tissue against the anvil as the firing bar severs the tissue.

12. The apparatus of claim 1, wherein each compressible member comprises a pair of legs and a bridge extending between the pair of legs.

13. The apparatus of claim 1, wherein each compressible member comprises a set of vertically extending fingers.

14. A staple cartridge for use with an end effector of a surgical stapler, the staple cartridge comprising:
(a) a cartridge body, wherein the cartridge body includes a cartridge deck, wherein the cartridge body further defines a plurality of staple openings passing through the cartridge deck;
(b) a plurality of staples associated with the plurality of staple openings;
(c) a plurality of staple drivers associated with the plurality of staple openings and the plurality of staples, wherein the staple drivers are configured to move toward the cartridge deck to drive the staples out of the staple openings; and
(d) a plurality of compressible features associated with at least some of the plurality of staple drivers, wherein the compressible features are movable with the associated staple drivers, wherein the compressible features are configured to deform toward the corresponding staple drivers in response to the compressible features pressing directly against tissue, wherein at least one of the compressible features includes first and second compressible arcuate members extending toward the cartridge deck, wherein a staple of the plurality of staples is configured to be laterally interposed between the first and second compressible arcuate members, wherein the first and second compressible arcuate members are arced at a central portion toward the cartridge deck.

15. The staple cartridge of claim 14, wherein the compressible features are configured to be driven through the staple openings and compress tissue against an anvil as the staples are driven through the tissue and into the anvil.

16. An apparatus comprising:
(a) a body;
(b) a shaft assembly extending distally from the body;
(c) an end effector, wherein the end effector comprises:
  (i) an anvil, and
  (ii) a lower jaw, wherein the anvil is pivotable toward the lower jaw to clamp tissue; and
(d) a staple cartridge coupled with the lower jaw, wherein the staple cartridge comprises:
  (i) a deck facing the anvil,
  (ii) a plurality of staples positioned in a plurality of staple openings formed through the deck, and
  (iii) a plurality of staple drivers configured to drive the staples out of the staple openings, wherein each staple driver of the plurality of staple drivers comprises:
    (A) a staple driver body, and
    (B) first and second compressible features extending from the staple driver body toward the anvil, wherein each staple laterally interposed between the first and second compressible features, wherein each of the first and second compressible features is configured to transition between a non-deflected configuration when not in contact with the tissue and a deflected configuration when in direct contact with the tissue, wherein the first compressible feature is independently compressible relative to the second compressible feature.

17. The apparatus of claim 16, wherein each pair of compressible features is configured to releasably grasp the corresponding staple associated with the pair of compressible features.

18. The apparatus of claim 14, wherein the first and second compressible arcuate members each comprise an elastomeric material.

19. The apparatus of claim 16, wherein each of the first and second compressible features each comprise an elastomeric material.

* * * * *